US012681574B2

(12) United States Patent
Remer et al.

(10) Patent No.: US 12,681,574 B2
(45) Date of Patent: Jul. 14, 2026

(54) METHOD AND APPARATUS FOR MULTI-DIMENSIONAL VESTIBULAR ELECTROPHYSIOLOGIC INTERFACING

(71) Applicant: LUNA LABS USA, LLC, Charlottesville, VA (US)

(72) Inventors: Joshua David Remer, Charlottesville, VA (US); Lawson Daniel Smith, Charlottesville, VA (US); Kelley Mitchell Virgilio, Charlottesville, VA (US); Eric Lancaster Breeden, Keswick, VA (US)

(73) Assignee: LUNA LABS USA, LLC, Charlottesville, VA (US)

( * ) Notice: Subject to any disclaimer, the term of this patent is extended or adjusted under 35 U.S.C. 154(b) by 157 days.

(21) Appl. No.: 18/670,017

(22) Filed: May 21, 2024

(65) Prior Publication Data

US 2026/0003431 A1      Jan. 1, 2026

(51) Int. Cl.
*G06F 3/01*          (2006.01)
*A61N 1/36*          (2006.01)

(52) U.S. Cl.
CPC .............. *G06F 3/015* (2013.01); *G06F 3/012* (2013.01); *A61N 1/36034* (2017.08); *A61N 1/36036* (2017.08)

(58) Field of Classification Search
CPC ...... G06F 3/012; G06F 3/015; A61N 1/36034
(Continued)

(56) References Cited

U.S. PATENT DOCUMENTS

| | | | | |
|---|---|---|---|---|
| 9,352,144 B2 * | 5/2016 | Paul | ................... | A61N 1/36031 |
| 2010/0152817 A1 | 6/2010 | Gillbe | | |

(Continued)

FOREIGN PATENT DOCUMENTS

| | | |
|---|---|---|
| JP | 2017-060581 | 3/2017 |
| KR | 10-2016-0106838 | 9/2016 |

OTHER PUBLICATIONS

G.N. Pradhan et al, "Visual Vestibular Conflict Mitigation in Virtual Reality Using Galvanic Vestibular Stimulation". Aerospace Medicine and Human Performance, vol. 93, No. 5, May 2022, pp. 406-414.

(Continued)

*Primary Examiner* — Calvin C Ma
(74) *Attorney, Agent, or Firm* — NIXON & VANDERHYE P.C.

(57) ABSTRACT

Neurological interfacing with a user is performed using by one or more hardware data processors including processing circuitry and memory that receives stimulation data from at least one data input source for stimulating two or three different axes of motion and processes the stimulation data to determine at least two of pitch, yaw, and roll parameters. Based on the at least two of the pitch, yaw, and roll parameters, at least two of a yaw current signal, a pitch current signal, and a roll current signal are determined. The at least two of the yaw current signal, the pitch current signal, and the roll current signal are time-multiplexed modulated signals. A maximum current amplitude signal occurs at different times for the at least two of the yaw current signal, the pitch current signal, and the roll current signal. Output currents are generated based on the least two of the yaw current signal, the pitch current signal, and the roll current signal. The output currents are selectively applied to at least some electrodes positioned on the user's head to induce in the user at least two of a desired yaw (Continued)

Expected

Actual sensation, a desired pitch sensation, and a desired roll sensation. Multiple relays are provided with each relay coupled to a corresponding current source and configured to selectively disconnect the corresponding current source from delivering a stimulation current to a corresponding electrode when the stimulation scenario requires that one or more electrodes be disconnected.

38 Claims, 24 Drawing Sheets

(58) Field of Classification Search
USPC .......................................................... 345/156
See application file for complete search history.

(56) References Cited

U.S. PATENT DOCUMENTS

| | | | |
|---|---|---|---|
| 2011/0029045 A1* | 2/2011 | Cevette ................. | A61N 1/323 |
| | | | 607/2 |
| 2012/0277835 A1 | 11/2012 | Della Santina et al. | |
| 2014/0127666 A1* | 5/2014 | Cevette ................ | A61N 1/3603 |
| | | | 434/365 |
| 2016/0262608 A1 | 9/2016 | Krueger | |
| 2017/0165481 A1* | 6/2017 | Menon ............... | A61N 1/36139 |
| 2021/0046312 A1 | 2/2021 | McKeown | |
| 2021/0283400 A1 | 9/2021 | Hamner et al. | |
| 2021/0290958 A1* | 9/2021 | McKeown ............ | A61M 21/02 |
| 2021/0322772 A1* | 10/2021 | Ramos De Miguel ...................... | |
| | | | A61F 11/04 |

OTHER PUBLICATIONS

G.N. Pradhan et al, "Generating Flight Illusions Using Galvanic Vestibular Stimulation in Virtual Reality Flight Simulations" Frontiers in Neuroergonomics, vol. 3, Article 883962, Apr. 26, 2022, pp. 1-9.

C. Groth et al, "Omnidirectional Galvanic Vestibular Stimulation in Virtual Reality" IEEE Transactions on Visualization and Computer Graphics, Feb. 2022, pp. 1-12.

K. Aoyama et al, "Four-pole galvanic vestibular stimulation causes body sway about three axes" Scientific Reports, May 11, 2015, pp. 1-8.

M.J. Cevette et al, "Electrogastrographic and Autonomic Responses During Oculovestibular Recoupling in Flight Simulation" Aviation, Space, and Environmental Medicine, vol. 85, No. 1, Jan. 2014, pp. 15-24.

V. Dilda et al, "Central Adaptation to Repeated Galvanic Vestibular Stimulation: Implications for Pre-Flight Astronaut Training" PLoS One, vol. 9, Issue 11, Nov. 19, 2014, pp. 1-7.

M.J. Cevette et al, "Oculo-Vestibular Recoupling Using Galvanic Vestibular Stimulation to Mitigate Simulator Sickness" Aviation, Space, and Environmental Medicine, vol. 83, No. 6, Jun. 2012, pp. 549-555.

V. Dilda et al, "Tolerance to Extended Galvanic Vestibular Stimulation: Optimal Exposure for Astronaut Training" Aviation, Space, and Environmental Medicine, vol. 82, No. 8, Aug. 2011, pp. 770-774.

S.T. Moore et al, "Galvanic Vestibular Stimulation as an Analogue of Spatial Disorientation After Spaceflight" Aviation, Space, and Environmental Medicine, vol. 82, No. 5, Section I, May 2011, pp. 535-542.

J.M. DeSantana et al, "Effectiveness of Transcutaneous Electrical Nerve Stimulation for Treatment of Hyperalgesia and Pain" Current Rheumatology Report, Dec. 2008.

K.A. Sluka et al, "Transcutaneous Electrical Nerve Stimulation: Basic Science Mechanisms and Clinical Effectiveness" The Journal of Pain, vol. 4, No. 3, Apr. 2003, pp. 109-121.

D.L. Wardman et al, "What does Galvanic Vestibular Stimulation Stimulate" Advances in Experimental Medicine and Biology, vol. 508, 2002, pp. 119-128.

International Search Report and Written Opinion of the International Searching Authority for PCT/US2024/030422 mailed Aug. 27, 2024, 27 pages.

* cited by examiner

METHOD AND APPARATUS FOR MULTI-DIMENSIONAL VESTIBULAR ELECTROPHYSIOLOGIC INTERFACING

GOVERNMENT RIGHTS

This invention was made with government support under contract number 140D0422C0053 awarded by DARPA and under NASA Ph 1 SBIR 80NSSC21C0256 awarded by NASA. The government has certain rights in the invention.

INTRODUCTION

Improving the interface between humans and machines is an ongoing need and challenge. This includes machine interfacing with the human nervous system, referred to as neurological or human-machine interfacing. Continued increases and improvements in the dimensionality of human-machine interfacing are desired. Dimensionality refers to multiple spatial dimensions. One example includes the familiar x, y, and z multiple spatial axes. Kinematics describes the motion of points, bodies (objects), and systems of bodies (groups of objects) using the geometry of a body and determining the position, velocity, and acceleration of the body or a part of the body.

The vestibular system is a sensory system that creates a sense of balance and spatial orientation for the purpose of coordinating movement with balance. Movements consist of rotations and translations, and in addition to receiving visual data and motion-related proprioceptive inputs from across the body, the vestibular system includes two components: the semicircular canals, which indicate rotational movements, and otolith organs that sense linear accelerations. The vestibular system sends signals to the muscles that keep an animal, e.g., a human, upright and in a posture required to enable an animal to maintain its desired position in space.

One type of human-machine interfacing is multi-dimensional or multi-axis vestibular stimulation in which electrodes are placed around the circumference of the head of a person and small amounts of electrical current (e.g., less than 10 mA) are injected into the person's head via the electrodes. These small currents may alter the membrane voltage potentials of the semicircular canals of the inner ear causing the sensation of motion to a user. The semicircular canal system detects rotational movements. Multidimensional vestibular interfacing can be used to reduce simulator sickness induced by virtual reality headsets, increase a sense of presence during virtual simulations, simulate and train for spatial disorientation, and treat vestibular upset or deficiency.

There are technical challenges associated with linking environmental kinematic (motion) signals to a visual display of a simulated environment. In multidimensional vestibular interfacing applications, (an example of neurological interfacing), there is a technical challenge associated with using environmental kinematic signals to accurately generate disorienting signals to a human to simulate a real situation in a virtual environment, e.g., a virtual reality (VR) environment, an augmented reality environment (AR), etc. Known hardware and methods for multidimensional vestibular interfacing applications do not accurately generate and deliver the sensations required for three-dimensional, concurrent vestibular stimulation. For example, known hardware does not provide sufficient control over individual pathways to accurately perform stimulation in all of the axes in multi-axial stimulation. Another technical challenge is that known approaches to three-dimensional real-time stimulation conflict with principles and behaviors of electrophysiology. For example, existing three-dimensional stimulation technologies cannot work for certain input combinations of axial stimulations. This results in an inability to generate precise currents at each electrode used in the system that reduces the accuracy and efficacy of the stimulation.

SUMMARY

These vestibular interfacing technical challenges, and other neurologic human-machine interfacing technical challenges, are solved using stimulation technology described in this application.

Some example embodiments provide a method for neurological interfacing with a user performed using one or more hardware data processors including processing circuitry and memory to perform the following steps: receiving stimulation data from at least one data input source for stimulating two or three different axes of motion; processing the stimulation data to determine at least two of pitch, yaw, and roll parameters; based on the at least two of the pitch, yaw, and roll parameters, determining at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal; generating output currents based on the at least two of the yaw current signal, the pitch current signal, and the roll current signal; and applying the output currents to each of multiple electrodes positioned on the user's head to induce in the user at least two of a desired yaw sensation, a desired pitch sensation, and a desired roll sensation.

The at least two of the yaw current signal, the pitch current signal, and the roll current signal are determined in order to reduce or avoid undesired electrical voltage gradients from being produced between two or more of the electrodes when applying the output currents to the electrodes positioned on the user's head.

In some example implementations, feedback information may be based on user motion, and the stimulation data and the feedback information may be processed to determine the at least two of the pitch, yaw, and roll parameters.

In some example implementations, two signals of the yaw current signal, the pitch current signal, and the roll current signal may have the same or similar time-multiplexed modulated signals that at least substantially overlap in time, and the other signal of the yaw current signal, the pitch current signal, and the roll current signal does not substantially overlap the two signals in time. A time-index duty cycle for the two signals may be for example 50% of a full cycle and a time-index duty cycle for the other signal may be for example 50% of a full cycle.

In some example implementations, a stimulation current may be calculated for each of the two signals based on a physio-electric circuit model used to calculate current sinking and sourcing at each of the multiple electrodes positioned on the user's head based on predetermined currents to be generated in each of the two signals. If a largest stimulation current of the two signals is determined to be below or equal to a threshold value, then a lesser of the two signals is eliminated before output currents are generated. If a largest stimulation current of the two signals is determined to be above a threshold value, then the generated output currents is converted to a current vector at each of the multiple electrodes, and based on the current vector at each of the multiple electrodes, an excess residual current is determined and a lesser of the two signals is eliminated before the generating output currents to reduce residual current.

In some example implementations, the maximum current amplitude signal occurs at different times for each of at least two of the yaw current signal, the pitch current signal, and the roll current signal such that respective maximum current amplitude signals for each of the at least two of the yaw current signal, the pitch current signal, and the roll current signal do not substantially overlap in time. A time-index duty cycle for each of the yaw current signal, the pitch current signal, and the roll current signal may for example be approximately one third of a full cycle.

In some example implementations, the stimulation data may be received from at least one of: a simulated environment, a memory storing pre-recorded, time-aligned visual and kinematic data, an inceptor, a smart device, and a medical device. The user may wear a head-mounted display and the method further comprises providing external visual input to the head-mounted display from at least one of the simulated environment, the memory storing pre-recorded, time-aligned visual and kinematic data, the inceptor, the smart device, and the medical device. If stimulation data is provided from a simulated environment, the stimulation data including angular velocity data for processing. The head-mounted display may provide head angular position data. The angular velocity data and the head angular position data may then be processed to determine the at least two of pitch, yaw, and roll parameters. Alternatively or in addition, the stimulation data from the memory may include pre-recorded, time-aligned visual and kinematic data which is processed to provide angular velocity data. The angular velocity data and the head angular position data may be processed to determine the at least two of pitch, yaw, and roll parameters. Alternatively or in addition, the stimulation data may be from the inceptor which provides interceptor vector magnitude data for processing to determine the at least two of pitch, yaw, and roll parameters.

In some example implementations, the at least two of pitch, yaw, and roll parameters may be transformed to generate an illusory vestibular signal that is based on an analytical model of how the human vestibular system adapts to constant angular velocity.

Some example embodiments provide a system for neurological interfacing with a user that includes one or more hardware data processors including processing circuitry and memory. The one or more hardware data processors are configured to: receive stimulation data from at least one data input source for stimulating two or three different axes of motion; process the stimulation data to determine at least two of pitch, yaw, and roll parameters; based on the at least two of the pitch, yaw, and roll parameters, determine at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal; generate output currents based on the least two of the yaw current signal, the pitch current signal, and the roll current signal; and apply the output currents to each of multiple electrodes positioned on the user's head to induce in the user at least two of a desired yaw sensation, a desired pitch sensation, and a desired roll sensation.

Some example embodiments provide for a system for neurological interfacing with a user that includes: an interface configured to receive output current values from the one or more hardware data processors corresponding to at least two of a yaw current signal, a pitch current signal, and a roll current signal, the one or more hardware data processors configured to communicate with the interface; one or more control processors configured to communicate with the interface; multiple current sources, each current source corresponding to and configured to provide a stimulation current to a stimulation electrode positioned on a user's head based on a corresponding one of the output current values; and multiple relays, each relay coupled to a corresponding one of the current sources and configured to selectively disconnect the corresponding current source from delivering a stimulation current to a corresponding electrode when a stimulation scenario requires that one or more electrodes be disconnected. The one or more control processors is configured to apply a stimulation current to at least some of multiple electrodes positioned on the user's head to induce in the user at least two of a desired yaw sensation, a desired pitch sensation, and a desired roll sensation.

In some example implementations, multiple fuses may be provided. Each fuse may be located between a corresponding one of the current sources and a corresponding electrode to protect against delivering a current to the user in excess of a maximum current value. One or more optoisolators may further be used to isolate signals provided to the one or more control processors and to the multiple relays.

Some example embodiments provide for a non-transitory, computer readable storage medium storing program instructions, which when executed by one or more hardware data processors, cause the one or more hardware data processors to perform the following method for neurological interfacing with a user: receiving stimulation data from at least one data input source for stimulating two or three different axes of motion; processing the stimulation data to determine at least two of pitch, yaw, and roll parameters; based on the at least two of the pitch, yaw, and roll parameters, determining at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal; generating output currents based on the at least two of the yaw current signal, the pitch current signal, and the roll current signal; and applying the output currents to each of multiple electrodes positioned on the user's head to induce in the user at least two of a desired yaw sensation, a desired pitch sensation, and a desired roll sensation.

Some example embodiments provide multi-axis neurological stimulation technology that is not restricted to direct-current-based Galvanic Vestibular Stimulation (GVS). Rather, the technology employs frequency-encoded processes that provide multi-axis neurological stimulation that is not galvanostatic.

Some example embodiments provide technology in a Three-Axis Wearable Adaptive Vestibular Stimulation (3WAVeS) system.

This Summary is provided to introduce a selection of concepts that are further described below in the Detailed Description. This Summary is intended neither to identify key features or essential features of the claimed subject matter, nor to be used to limit the scope of the claimed subject matter; rather, this Summary is intended to provide an overview of the subject matter described in this document. Accordingly, it will be appreciated that the above-described features are merely examples, and that other features, aspects, and advantages of the subject matter described herein will become apparent from the following Detailed Description, Figures, and Claims.

BRIEF DESCRIPTION OF THE FIGURES

These and other features and advantages will be better and more completely understood by referring to the following detailed description of example non-limiting illustrative embodiments in conjunction with the drawings of which.

DETAILED DESCRIPTION OF EXAMPLE EMBODIMENTS

Figure 1:
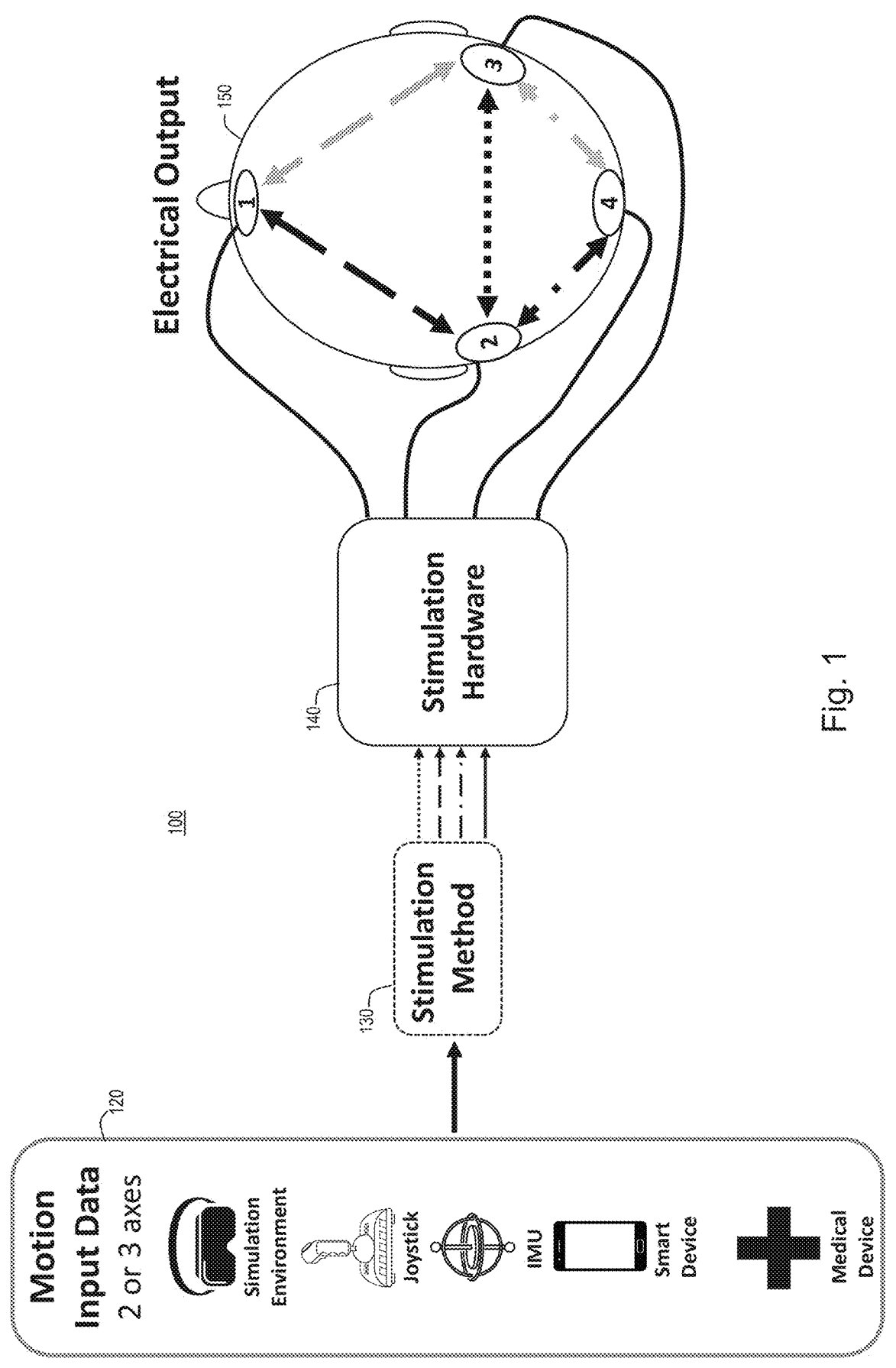
FIG. 1 shows a system for multi-axis or multidimensional vestibular interfacing vestibular interfacing.

Specific embodiments are shown by way of example in the drawings and will herein be described in detail. It should be understood, however, that the drawings and detailed description are not intended to limit the claims to the particular embodiments disclosed, even where only a single embodiment is described with respect to a particular feature. On the contrary, the intention is to cover all modifications, equivalents and alternatives that would be apparent to a person skilled in the art having the benefit of this disclosure. Examples of features provided in the disclosure are intended to be illustrative rather than restrictive unless stated otherwise.

As used throughout this application, the word "may" is used in a permissive sense (i.e., meaning having the potential to), rather than the mandatory sense (i.e., meaning must). Similarly, the words "include," "including," and "includes" mean including, but not limited to.

FIG. 1 shows an example system for multi-dimensional vestibular interfacing that includes four primary elements as shown in the example system 100 for multi-axis or multi-dimensional vestibular interfacing including motion input (sometimes referred to as kinematic) input data 120 for two or three dimensions or axes, such as yaw inputs, pitch inputs, and roll inputs. The motion input data may be provided or come from one or more sources with examples including one or more simulation environments, joysticks, inertial measurement units (IMUs), smart devices, medical devices, and others. The multi-dimensional vestibular interfacing system 100 further includes one or more stimulation methods or a set of algorithms 130 that receives the motion input data 120 and stimulation hardware 140 which performs or executes the stimulation methods or a set of algorithms 130 using the motion input data 120. The electrical outputs from the stimulation hardware 140 are sent to electrodes, e.g. 1-4, on a user's head 150. The stimulation method or set of algorithms 130 performed or executed by the stimulation hardware 140 converts two or three axes of motion input data 120 into vestibular stimulation signals that evoke vestibular sensations via the electrodes.

To convert the motion input data 120 into one or more useful vestibular sensations, the motion input data 120 is mapped to an appropriate series of electrodes such as the four electrodes 1, 2, 3, and 4 shown in FIG. 1. This mapping is performed by the stimulation method(s) or set of algorithms 130 to electrically or temporally isolate signals that would cause stimulation conflicts if applied concurrently. In FIG. 1, a yaw current input is mapped to electrodes 2 and 3 as shown in FIG. 1 shown with a dotted line. A pitch current input is mapped (dashed lines) between electrode 1 and electrode 2 and electrode 1 and electrode 3, and a roll current input is mapped between electrode 2 and electrode 4 shown with dot-dashed lines and electrode 3 and electrode 4 shown with dot-dashed lines.

Figures 2A, 2B, 3:
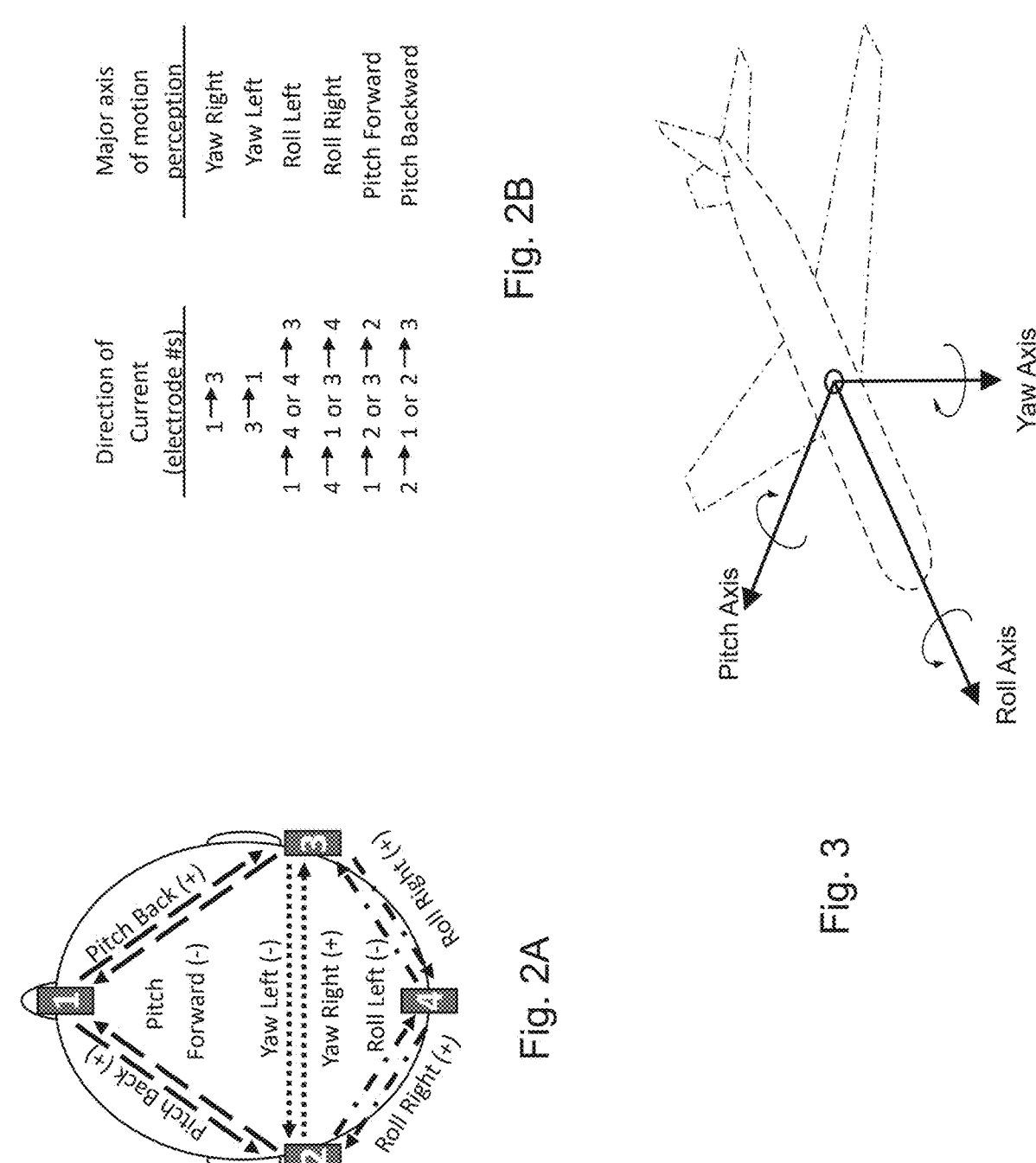
FIGS. 2A-2B illustrate vestibular sensation and electrode current pathways relative to the head of the user being stimulated.
FIG. 3 illustrates yaw, pitch, and roll axes in the example of an airplane.

FIGS. 2A-2B illustrate example vestibular sensation and electrode current pathways relative to the head of the user being stimulated that includes yaw right, yaw left, pitch forward, pitch back, roll left, and roll right current applications to the head via the four electrodes. FIG. 3 shows example yaw, pitch, and roll axes for an airplane. To stimulate a "pitch back" sensation for the user, there needs to be a positive voltage drop or gradient from electrode 1 to 2 or electrode 1 to 3. To stimulate a "pitch forward" sensation, a positive voltage drop or gradient (+ to −) must be applied between electrodes 2 to 1 or electrodes 3 to 1. To stimulate a "yaw left" sensation, a positive voltage drop or gradient must be applied between electrode 3 to electrode 2. To stimulate a "yaw right" sensation, a positive voltage drop or gradient must be applied between electrode 2 to electrode 3. To stimulate a "roll left" sensation, a positive voltage drop or gradient must be applied between electrode 2 to electrode 4 or a positive voltage gradient must be applied between electrode 4 to electrode 3. To stimulate a "roll right" sensation, a positive voltage drop or gradient must be applied between electrode 3 to electrode 4 or a positive voltage drop must be applied between electrode 4 to electrode 2.

In a simple, one-dimensional stimulation used in known methods, a yaw input could be directly mapped to Electrodes 2 and 3 as shown in FIG. 2. In a higher complexity stimulation where two or more axes are used, some electrodes within the system may be used for multiple axes of stimulation. A problem arises that when input axes are simply directly mapped to electrode outputs, certain combinations of multi-axis inputs may require combinations of electrical inputs that are not physically possible to provide, which results in unintended vestibular sensations being generated. Hardware used in known systems does not provide sufficient control over individual electrical pathways to perform all multi-axial stimulation accurately. Furthermore, the input-to-electrode direct mapping method used in known systems for multi-dimensional real-time stimulation can result in undesired electrical gradients which decreases the efficacy and utility of the stimulation.

Figure 4:
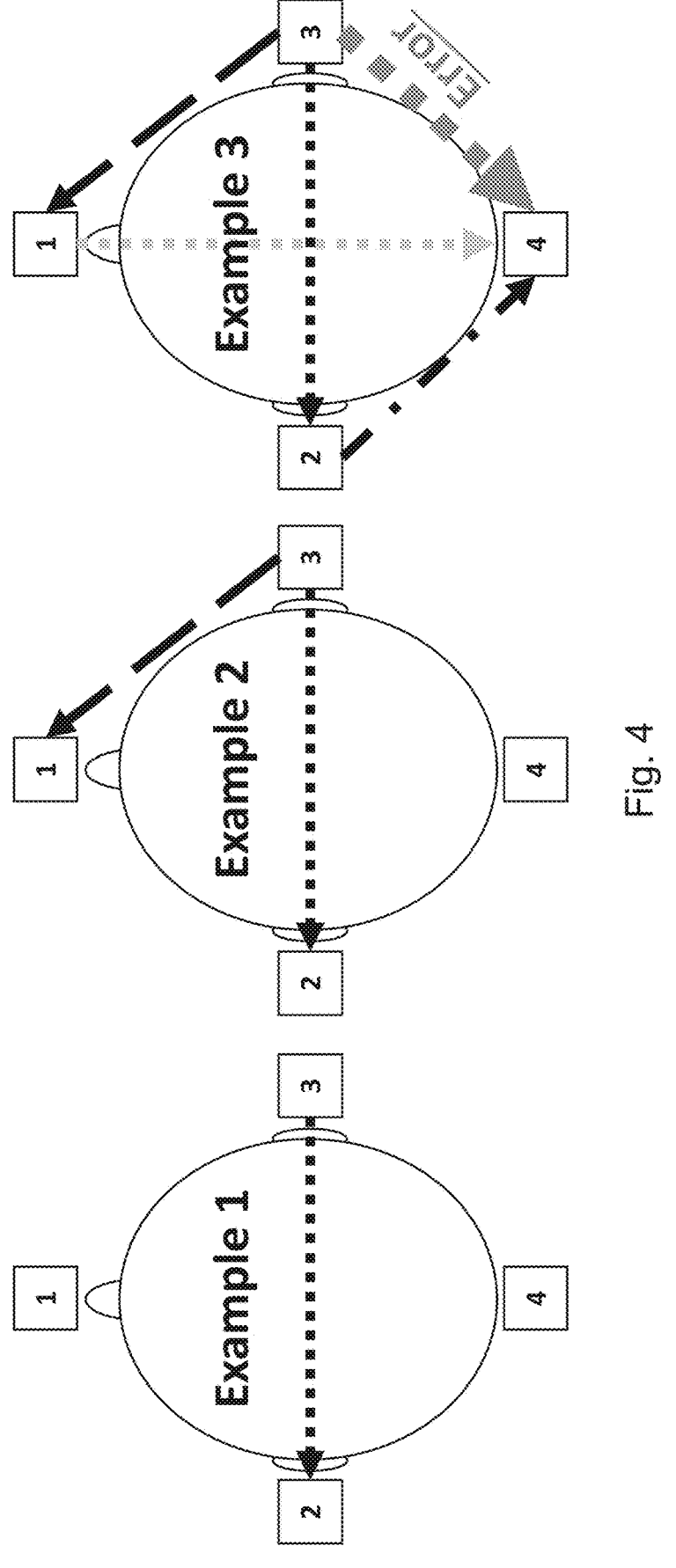
FIG. 4 visual depicts examples described in Table 1.

Table 1 below shows an example of voltage application to electrodes for a select set of desired vestibular sensations using the direct mapping multidimensional vestibular interfacing approach. FIG. 4 visually depicts examples 1-3 described in Table 1.

TABLE 1

| Exam-ple | Voltage Application | | | | Current Flow | Paradigm Application |
|---|---|---|---|---|---|---|
| | E1 | E2 | E3 | E4 | | |
| 1 | X | O | +1 | X | Electrode 3 --> Electrode 2 | Yaw Left |
| 2 | O | O | +1 | X | Electrode 3 --> Electrode 2 | Yaw Left, |
| | | | | | Electrode 3 --> Electrode 1 | Pitch Forward |
| 3 | O | O | +1 | −1 | Electrode 3 --> Electrode 2 | Yaw Left, |
| | | | | | Electrode 3 --> Electrode 1 | Pitch |
| | | | | | Electrode 2 --> Electrode 4 | Forward, |
| | | | | | Electrode 1 --> Electrode 4 | Roll Left |
| | | | | | Electrode 3 --> Electrode 4 | (ERROR) |

Based on Example 1 in Table 1 and FIG. 4, a successful yaw left sensation can be generated as can a Yaw Left, Pitch Forward sensation as shown in Example 2. However, in Example 3, a fundamental error prevents successful sensations from being generated in all three axes. In this case, the need to generate a Roll Left sensation means that current must be driven from electrode 2 to electrode 4, which means that electrode 4 is set at a negative voltage. However, this creates a doubly strong electrical gradient from electrode 3 to electrode 4, which results in an enhanced roll right sensation which is much larger than the desired roll left sensation. Although Example 3 can also be alternately structured due to the duplicate stimulation locations of pitch and roll, the end erroneous effect is the same. Additionally, a gradient between electrode 1 and electrode 4 is formed, but that gradient is not known to correlate with any perceived sensation.

Table 2 below is a state table that shows the mappings for possible inputs in three axes using the direct mapping multidimensional vestibular interfacing approach described above with respect to FIGS. 2-4.

TABLE 2

| Number of Active Stimulation Axes | | | Axial Input | | | Electrode Potential (−, O, +, or X {Removed}) | | | | Conflicting |
|---|---|---|---|---|---|---|---|---|---|---|
| 1 | 2 | 3 | Yaw | Pitch | Roll | E1 | E2 | E3 | E4 | |
| | | X | L | F | L | | | | | Yes |
| | X | | L | F | N | − | − | + | X | |
| | | X | L | F | R | − | − | + | O | |
| | X | | L | N | L | | | | | Yes |
| X | | | L | N | N | X | − | + | X | |
| | X | | L | N | R | X | − | + | O | |
| | | X | L | B | L | | | | | Yes |
| | X | | L | B | N | + | − | + | X | |
| | | X | L | B | R | + | − | + | O | |
| | X | | N | F | L | − | + | X | − | |

TABLE 2-continued

| Number of Active Stimulation Axes | | | Axial Input | | | Electrode Potential (−, ○, +, or X {Removed}) | | | | |
|---|---|---|---|---|---|---|---|---|---|---|
| 1 | 2 | 3 | Yaw | Pitch | Roll | E1 | E2 | E3 | E4 | Conflicting |
| X | | | N | F | N | − | + | + | X | |
| | X | | N | F | R | − | X | + | − | |
| X | | | N | N | L | X | + | − | ○ | |
| X | | | N | N | N | ○ | ○ | ○ | ○ | |
| X | | | N | N | R | X | − | + | ○ | |
| | X | | N | B | L | + | X | − | + | |
| X | | | N | B | N | + | − | − | X | |
| | X | | N | B | R | + | − | X | + | |
| | | X | R | F | L | − | + | − | ○ | |
| | X | | R | F | N | − | + | − | X | |
| | | X | R | F | R | | | | | Yes |
| | X | | R | N | L | X | + | − | ○ | |
| X | | | R | N | N | X | + | − | X | |
| | X | | R | N | R | | | | | Yes |
| | | X | R | B | L | + | + | − | ○ | |
| | X | | R | B | N | + | + | − | X | |
| | | X | R | B | R | | | | | Yes |

Yaw Inputs: Left (L), Neutral (N), Right (R)
Pitch Inputs: Forward (F), Neutral (N), Back (B)
Roll Inputs: Left (L), Neutral (N), Right (R)

All possible axial inputs given three axes of input are shown, and conflict (error) cases are identified in the rightmost column. Six of the 27 inputs generate a conflict (error) because of the interplay between the roll and yaw axes. In all cases where a roll and yaw are desired in the same direction, a conflict (error) is generated. Thus, the known multidimensional vestibular interfacing direct mapping approach cannot successfully generate all multi-axis stimulations accurately and as desired/intended.

Figure 5:
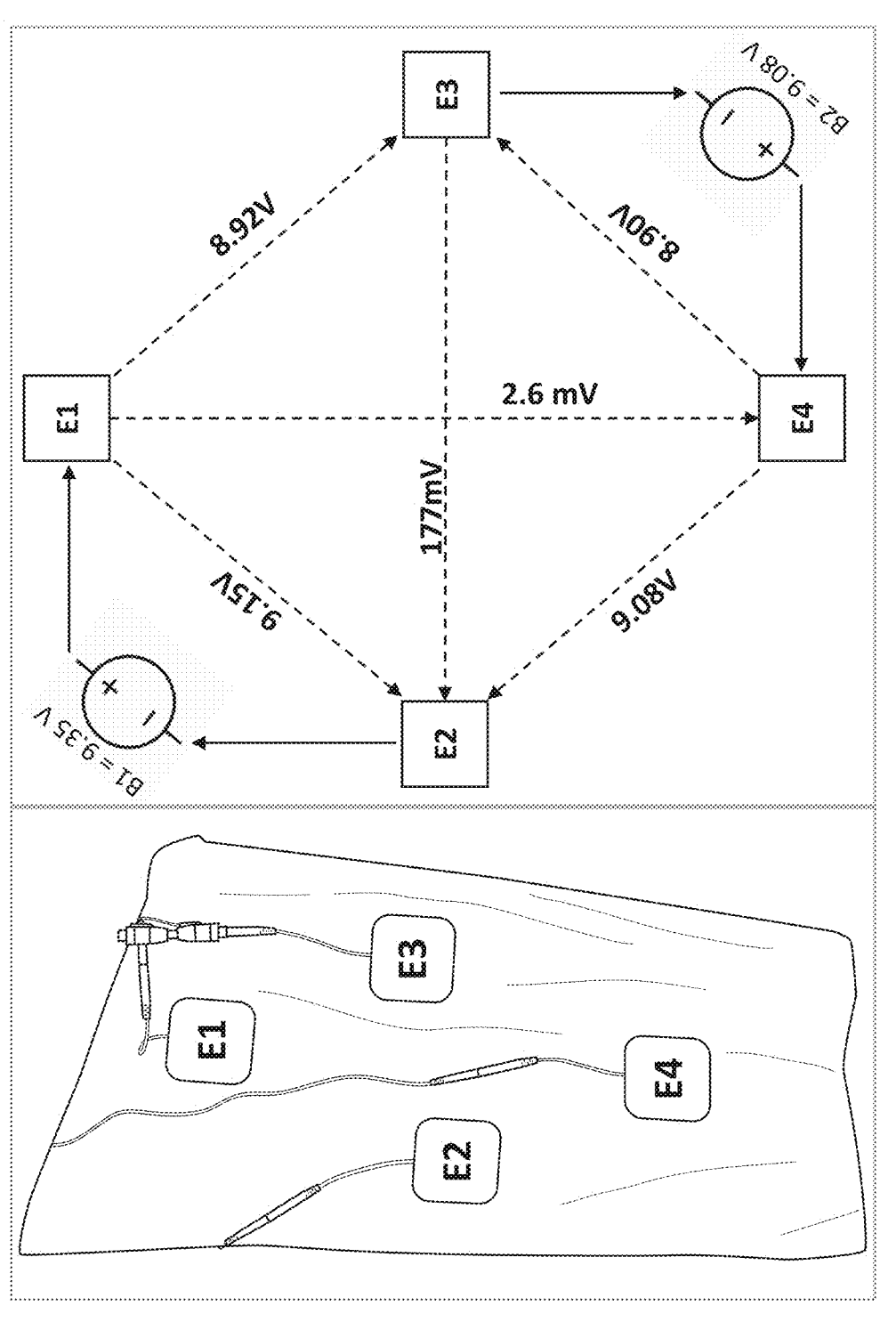
FIG. 5 shows an example experiment using porcine skin with DC power inputs that tested the known multidimensional vestibular interfacing approach and measured results of the experiment.

The inventors conducted an example experiment using a porcine skin substrate with DC power inputs to test the known multidimensional vestibular interfacing direct mapping approach and then measured results of the experiment. See the illustration of porcine skin to the left in FIG. 5 with electrodes E1-E4 placed on the surface of the skin at different locations. The right side of FIG. 5 shows two independent DC power sources on a porcine skin substrate each connected to a respective electrode pair. One DC power source generated 9.35 volts with its negative terminal connected to electrode E2 and its positive terminal to electrode E1. The other DC power source generated 9.08 volts with its negative terminal connected to electrode E3 and its positive terminal to electrode E4. Voltage was measured between each electrode pair combination, for a total of six measurements as shown. The electrode measurements were analyzed according to the known multidimensional vestibular interfacing direct mapping method, as if a Pitch Backward, Roll Left sensation was being applied. The net effect was a Pitch Backward gradient between E1-E2, and E1-E3, as well as a Roll Left gradient from E4-E3, and a Roll Right gradient from E4-E1. The interaction between independent power sources resulted in an undesired Roll gradient.

While a significant voltage drop was measured across the electrode pairs (E1-E2, E4-E3) connected to each power source, a similar voltage drop was measured between electrode pairs not connected to a single power source (E1-E3, E4-E2). This test result confirms that independent DC power sources do in fact interact and interfere, that the previously described issues where multi-axis stimulations may interfere are true, and that the known multidimensional vestibular interfacing method cannot accurately produce every case of multi-axis stimulation as intended, as voltage gradients can be formed between isolated power sources.

Figure 6:
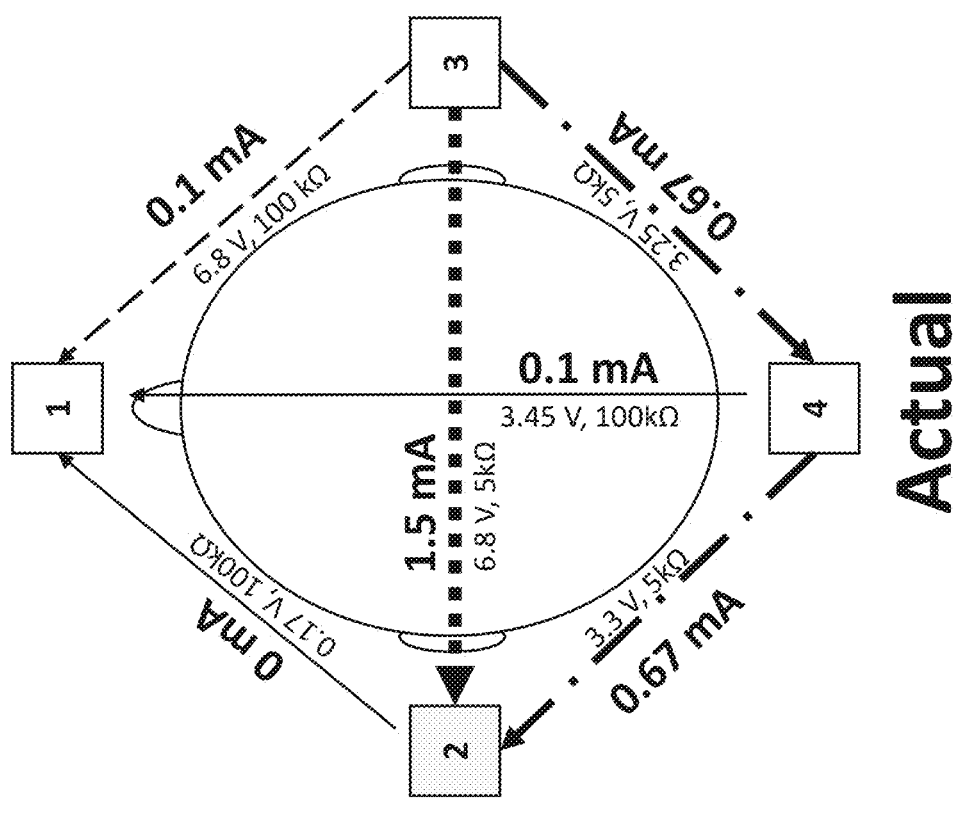
FIG. 6 shows electrical output from the known multidimensional vestibular interfacing approach comparing expected electrical pathways with actually measured electrical pathways.
Figure 6:
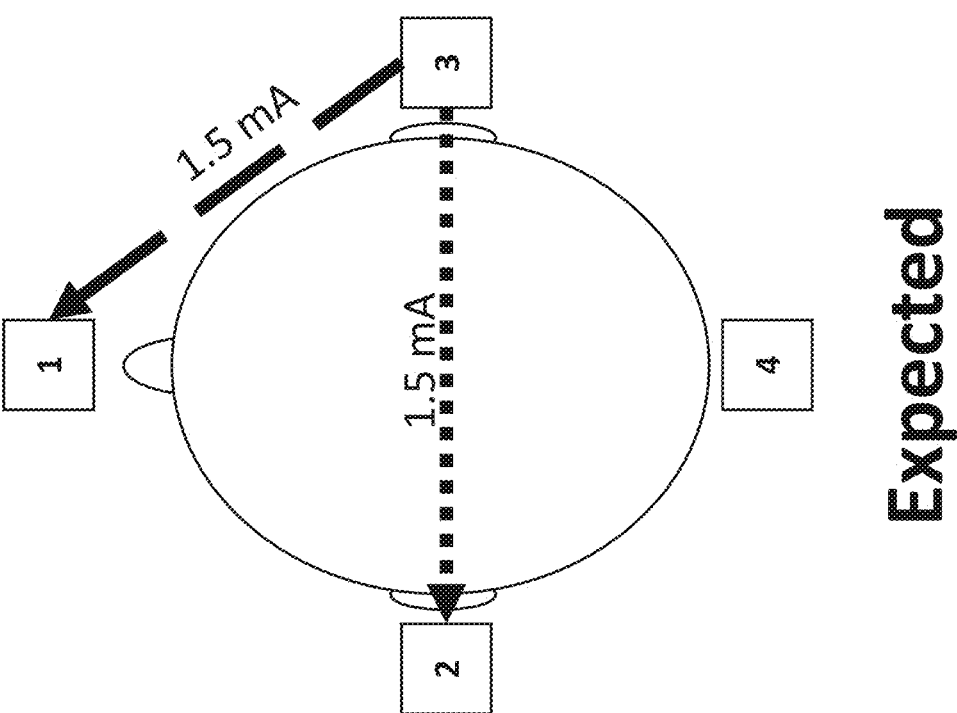

The inventors conducted a further experiment for the configuration in FIG. 5 using the known multidimensional vestibular interfacing direct mapping method and hardware during real-time multi-axis stimulations. Impedance and voltage drop were measured across each electrode pair, and current was subsequently calculated using Ohm's law. FIG. 6 shows electrical output from the known multidimensional vestibular interfacing direct mapping approach comparing expected electrical pathways with actually measured electrical pathways. Both the "expected" and "actual" electrical gradients between all possible pairs of electrodes that are formed during a yaw left, pitch forward scenario are shown. On the "expected" gradient side of FIG. 6, 1.5 mA of output current was selected in the hardware output for stimulation channel E3 to E1 and stimulation channel E3 to E2 as shown. However, the current selection is based on a nominal, non-changing impedance and is actually a voltage source, with current values correct at a nominal 5 kΩ impedance. It does not adapt to real-time impedance conditions in this experiment, where electrode E2 exhibits a much higher impedance (100 kΩ) than the impedance measures for the other electrodes (5 kΩ), which means that for a given voltage setting, the actual current output is not accurate. Although electrode E4 was not intended to be active in this further experiment, the hardware provided no mechanism to remove it. Even though E4 was selected to be inactive (0V) during the further experiment, it nevertheless was active in the sense that it functioned as an additional current source to electrode 2 and an additional current sink to electrode 3. Thus, while the intended generated signal was a yaw left, pitch forward, the actual primary sensation generated by the known multidimensional vestibular interfacing direct mapping method and hardware was a yaw left, roll right, which is an error and unintended.

The inventors identified two key technical challenges from these experiments. First, generated voltage/current outputs to the electrodes should be controlled in some way, e.g., with some type of feedback loop, to ensure accurate voltage gradient generation and subsequent current delivery. Second, electrodes not involved in the desired stimulation must be disconnected from a stimulation to prevent unintentional current sinking/sourcing. The Three-Axis Wearable Adaptive Vestibular Stimulation (3WAVeS) methods and hardware (described below) address and resolve both of these technical challenges by accurately generating voltage gradients and currents delivered to the electrodes and by providing for automatic disconnection of one or more electrodes via one or more relays.

The 3WAVeS system includes four primary components: backend software programs and data for the 3WAVeS system (referred to below simply as the 3WAVeS software), a user interface, stimulation computer program algorithms referred to herein as Neurologic Multi-Axis Paradigms for Stimulation (NeuroMAPS) algorithms, and 3WAVeS stimulation hardware circuitry. The 3WAVeS system takes multi-axis input data from one or more primary sources, with examples including but not limited to: real-time simulation environment(s), pre-recorded data, inceptor input, various types of devices. However, other sources of multi-axis input data may be used. The 3WAVeS system may be used, for example, to generate restorative vestibular sensations in connection with the desired environment and may also be used to generate illusory vestibular sensations to simulate spatially disorienting scenarios.

Figure 7:
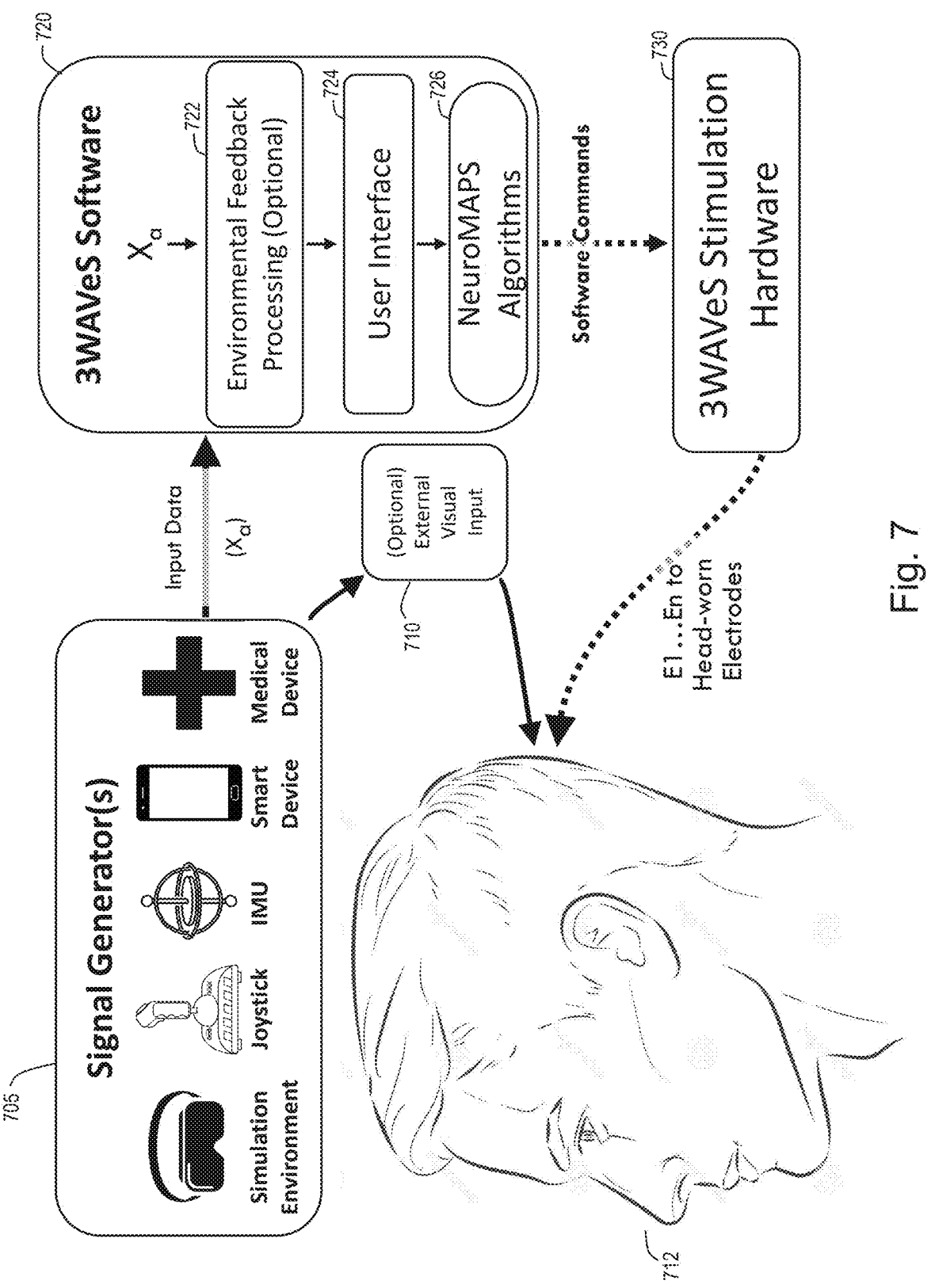
FIG. 7 shows an example embodiment of a Three-Axis Wearable Adaptive Vestibular Stimulation (3WAVeS) system.

FIG. 7 shows an example embodiment of a Three-Axis Wearable Adaptive Vestibular Stimulation (3WAVeS) system. Signal generator(s) 705 shows several example multi-axis input data signal generators including a simulation environment like a head mounted display, a camera or other device to provide recorded data, an inceptor device like a joystick that can be moved with a hand, one or more fingers, etc., an inertial measurement unit (IMU), a smart device like a smart phone, and/or a medical device that might include an IMU. Other signal generators may be used. The signals generated from 705 include multi-axis stimulation data $X_a$ which is input to the 3WAVeS software 720. The multi-axis stimulation input data may take different forms. For example, a simulation environment and/or a camera may be used to provide angular velocity as multi-axis stimulation input data. A joystick may provide axis, magnitude, and direction multi-axis stimulation input data for each of the pitch, yaw, and roll axes for each position the joystick is moved to. In healthcare applications, the input signal may be provided from an assistive device. For example, to aid vertigo sufferers, an inertial measurement unit may be used to generate "correct" vestibular signals for someone who is standing normally upright, which override the errant vertigo-linked signals which affect or even incapacitate the vertigo sufferer. Ultimately, input signals from one or more signal generators 705 are processed through the 3WAVeS software 720 to output desired vestibular sensation, which includes but is not limited to pitch, yaw, and roll sensations.

FIG. 7 also shows optional external visual input 710 may be provided to a user 712 in cases where this increased dimensionality is desired, such as a virtual reality simulation or entertainment environment. However, the external visual input 710 does not affect the vestibular stimulation.

The 3WAVeS software 720 may operate on any suitable computing platform, for example, on a PC or on a mobile device like a tablet, smartphone, or smartwatch. The 3WAVeS software 720 includes instructions and steps, which when executed or implemented by one or more data processors, e.g., CPUs, microprocessors, DSPs, ASICs, etc., included in the computing platform running the 3WAVeS software 720, converts the input data $X_a$ into software commands containing polarity and magnitude information for each electrode (E1-En) worn in the system. This signal is sent to the 3WAVeS Stimulation Hardware 730 which interprets the software commands and generates the appropriate current polarity and magnitude in each electrode (E1-En) in the system.

Figure 23:
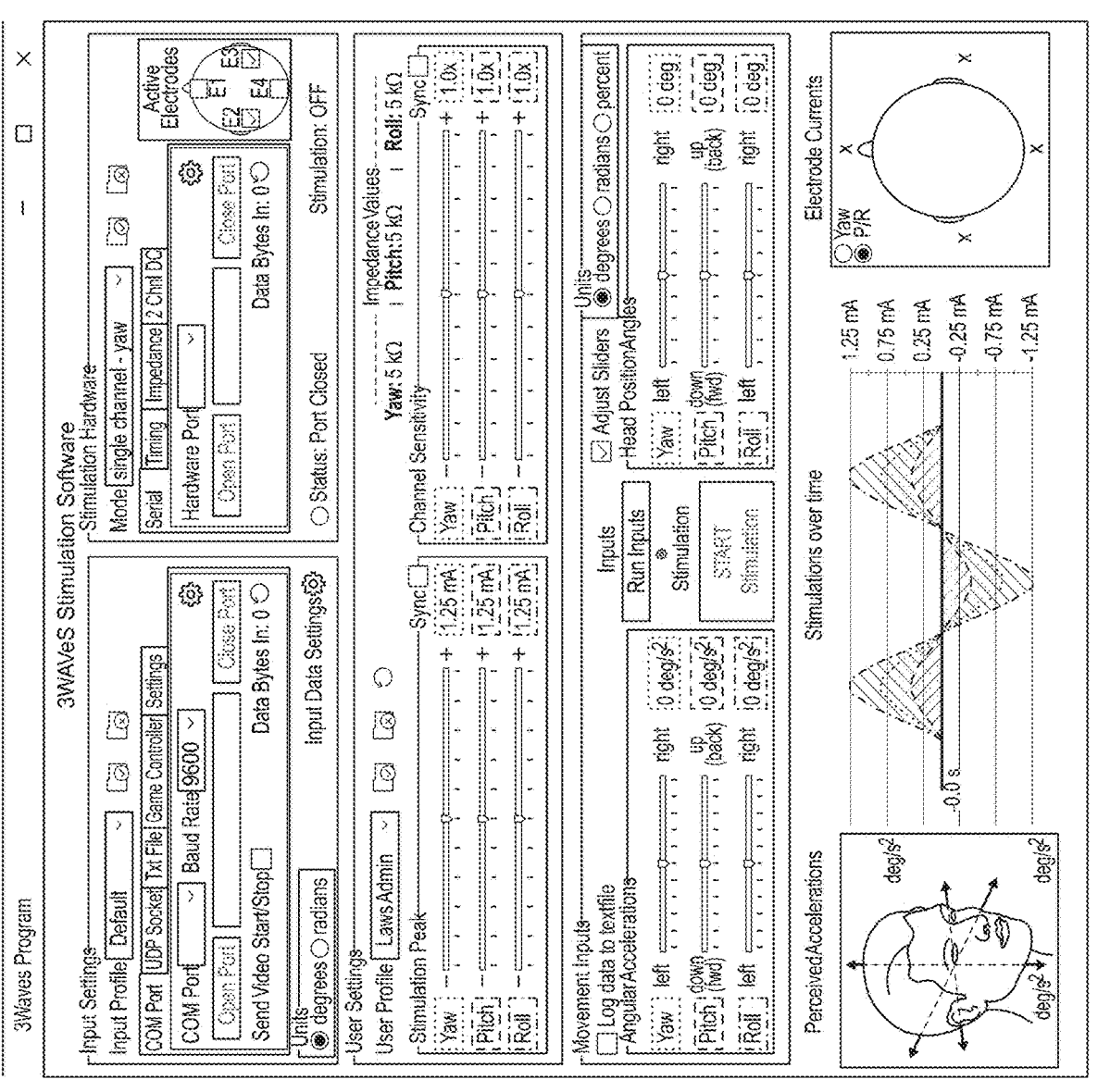
FIG. 23 is an example embodiment of a 3WAVeS graphical user interface.

The 3WAVeS software 720 contains several data processing blocks, including optional Environmental Feedback Processing 722, User Interface 724, and the NeuroMAPS Algorithms 726. The optional Environmental Feedback Processing 722 block allows the input signal $X_a$ to be modified by a real-time feedback data source. An example may be applying a rotation matrix to the input signal $X_a$ data using real-time angular position data from a user wearing a VR headset in a simulation, thus adaptively modifying the generated stimulation based on the user's angular position within a VR environment. Other embodiments of the 3WAVeS technology may not use Environmental Feedback Processing 722. The modified or unmodified signal is then further modified by the User Interface 724, in which a user can adjust various features of the signal and adjust and interact with multiple aspects of the 3WAVeS system operation in real time, including but not limited to: data input source, individual channel sensitivity, individual channel intensity scaling, user profile saving and loading, and real-time observation of stimulation parameters. An example user interface is shown in FIG. 23 and described below including examples of user modifications via multiple user-selectable settings accessible on the user interface.

The user interface software 724 outputs a digital command with magnitude and polarity for up to three axes which are processed according to analytical electrical and temporal modeling by the NeuroMAPS algorithms software 726 into digitally encoded command instructions that include current or voltage polarity and magnitude for each electrode worn on the user's head 712. The NeuroMAPS algorithms software 726 includes a comprehensive set of mathematical stimulation models, methods, or paradigms (detailed examples of which are described in conjunction with FIG. 12) used in converting multi-axis inputs into meaningful vestibular digital output commands. The NeuroMAPS algorithms software 726 performs mathematical and electrophysiologic circuit modeling to calculate the necessary current magnitude to be delivered to each electrode. The modeling may be real-time if real-time input is to be correlated to real-time output. Thus, the 3WAVeS software 720, when executing, executes processing algorithms on axial digital commands as adjusted according to the settings of the user interface software 724, and generates software commands provided to 3WAVeS Stimulation Hardware 730. An example of 3WAVeS Stimulation Hardware 730 is described below in conjunction with FIG. 24.

These commands are used by the 3WAVeS Stimulation Hardware 730 to generate the actual electrical currents to be transmitted to and through each of the electrodes (e.g., E1-E4) which are fixed on the user's head 712. The 3WAVeS Stimulation Hardware 730 may include multiple current-sources and receives digital input from the NeuroMAPS algorithms software 726 and uses precision timing, signal feedback, and multiple layers of safety devices to safely generate controlled currents. For example, if four electrodes are attached to the user's head, the NeuroMAPS algorithms software 726 safely generates controlled currents across 6 independent current pathways from 4 electrodes, or potentially more pathways. The current generated and applied to the electrodes can be DC current, or it can be AC current alternating at a frequency in a desired frequency range, e.g., 1 kHz-100 kHz.

Figure 8:
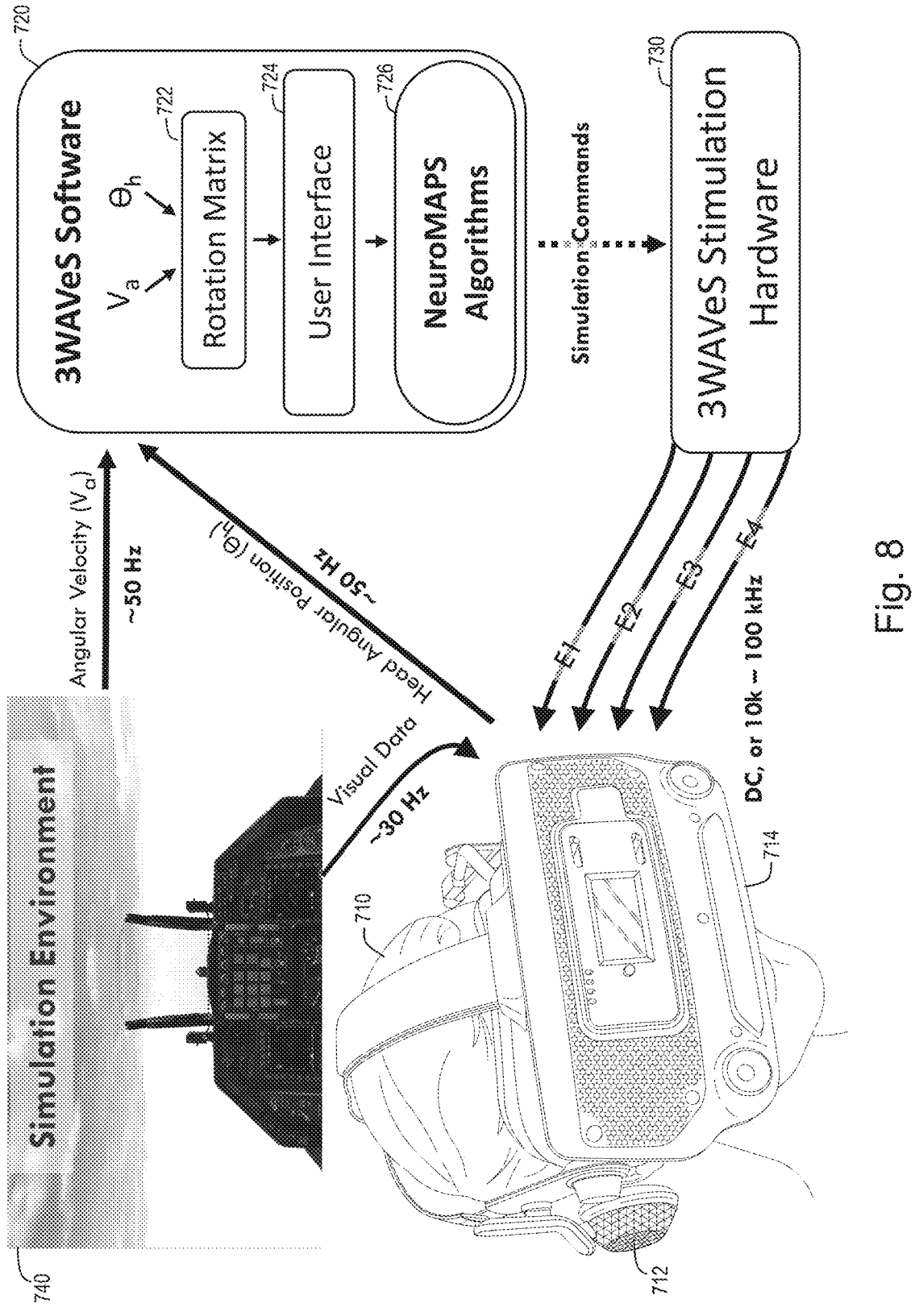
FIG. 8 shows an example embodiment of a mixed reality (MR)-linked 3WAVeS system using a simulation environment to provide visual data to a user.

FIG. 8 shows an example embodiment of the 3WAVeS system in a mixed reality (MR)-linked operational mode where 3WAVeS software 720 receives streamed kinematic input data in real time from both a simulation environment 740 and from a user's headset 714 worn on a user's head 710. Examples of a simulation environment include any virtual or mixed reality simulation environment. One example is a flight simulator. Initially, all of the relevant visual data from the simulation environment 740 is communicated to the headset 714 at a suitable data rate. The example shown in FIG. 8 is 30 Hz, but other rates may be used. The simulated environment 740 provides angular velocity data $V_a$ (one example type of kinematic data) of a simulated vehicle or avatar displayed in the simulation environment 740 to the 3WAVeS software 720. The example shown in FIG. 8 is a data rate of about 50 Hz. Other rates may be used. The user headset 714 provides head angular position data $\theta_h$ of the user's head position at different times (another example type of kinematic data) to the 3WAVeS software 720 at an example data rate of about 50 Hz. Again, other rates may be used.

Figure 12:
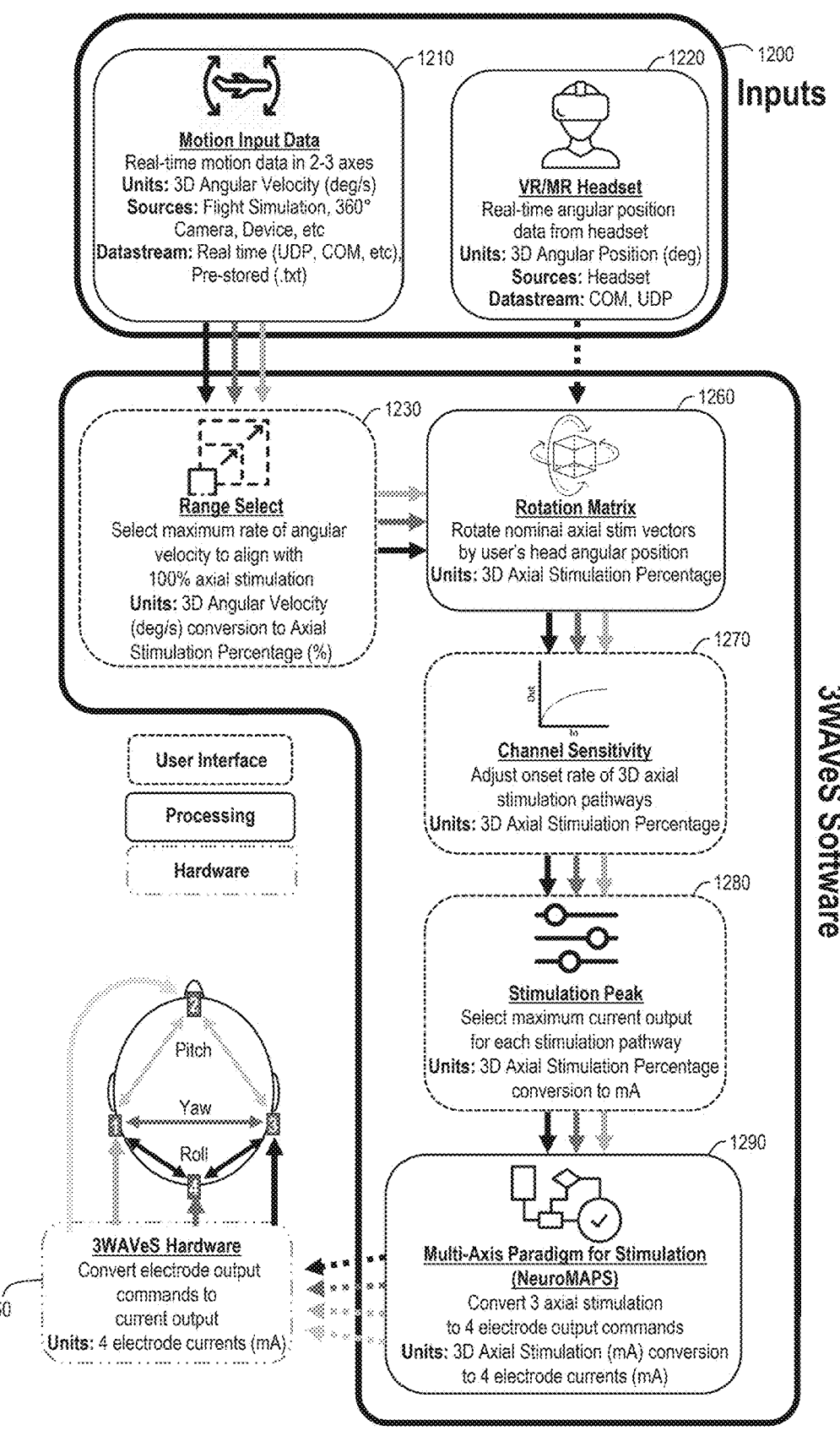
FIG. 12 shows an example embodiment of a flow diagram for operation of example embodiments of a 3WAVeS system.

The 3WAVeS software 720 includes instructions, which when executed or implemented by one or more data processors, e.g., CPUs, microprocessors, DSPs, ASICs, etc., included in the computing platform running the 3WAVeS software 720, processes the varied input data through several steps to result in stimulation commands for each electrode in the system, sent via software to the 3WAVeS stimulation hardware 730. The angular velocity data $V_a$ and the head angular position data $\theta_n$ are processed in a Rotation Matrix block 722 that generates perceived pitch, yaw, and roll motions, i.e., as perceived by the user engaging with the simulation environment. These perceived pitch, yaw, and roll motions are processed and modified via multiple user-selectable settings in the user interface block 724. The data stream is then processed through the NeuroMAPS Algorithms block 726 to result in stimulation commands for each electrode in the system. FIG. 12 demonstrates each of these blocks in more detail, and FIG. 15 demonstrates a set of possible NeuroMAPS algorithms. The processing by the 3WAVeS software 720 and the 3WAVeS stimulation hardware 730 of the angular velocity and head angular position stimulation input data is similar to the processing described for FIG. 7. The mixed reality-linked operational mode of the 3WAVeS system may be used, for example, in simulation-based training and can significantly enhance the sense of presence (i.e., the user's sense of being inside the simulated environment) and reduce motion sickness.

Figure 9:
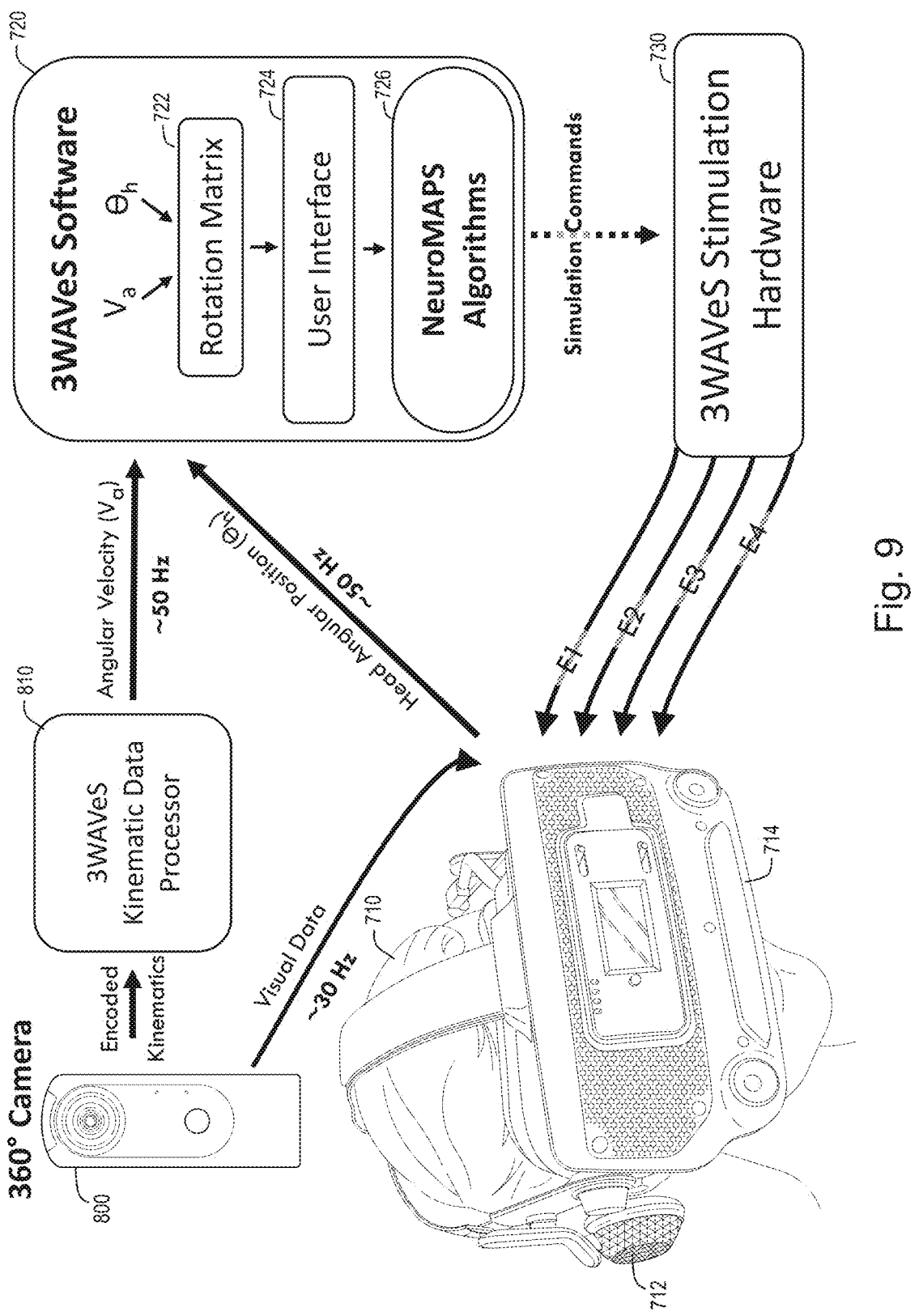
FIG. 9 shows an example embodiment of a 3WAVeS system that provides pre-recorded visual data, e.g., from a camera, to a user and to a 3WAVeS kinematic data processing subsystem.

FIG. 9 shows an example embodiment of the 3WAVeS system that is similar in many respects to that in FIGS. 7 and 8. Compared to the embodiment in FIG. 7, instead of using simulation environment kinematic input data, the embodiment of FIG. 9 uses pre-recorded visual and kinematic data inputs. A camera 800, e.g., a 360 degree camera, records and provides visual data of a real environment to the user headset 714 and motion (kinematics) data to 3WAVeS kinematic data processor 810 which may process position data to derive and generate angular velocity data $V_a$. The processing by the 3WAVeS software 720 of the angular velocity data $V_a$ and the head angular position data $\theta_h$ and the 3WAVeS stimulation hardware 730 of the output software commands is similar to that described for FIG. 8. This pre-recorded visual and motion (kinematic) input data operational mode of the 3WAVeS system is useful, for example, for research because the same visual stimuli can be repeatedly applied and for virtual reality (VR)-entertainment where pre-recorded visual and kinematic data are often used. There are other example applications for this mode, such as in cinema and amusement rides, and other digital devices may be used to generate the temporally aligned visual and motion (kinematic) data for this mode.

Figure 10:
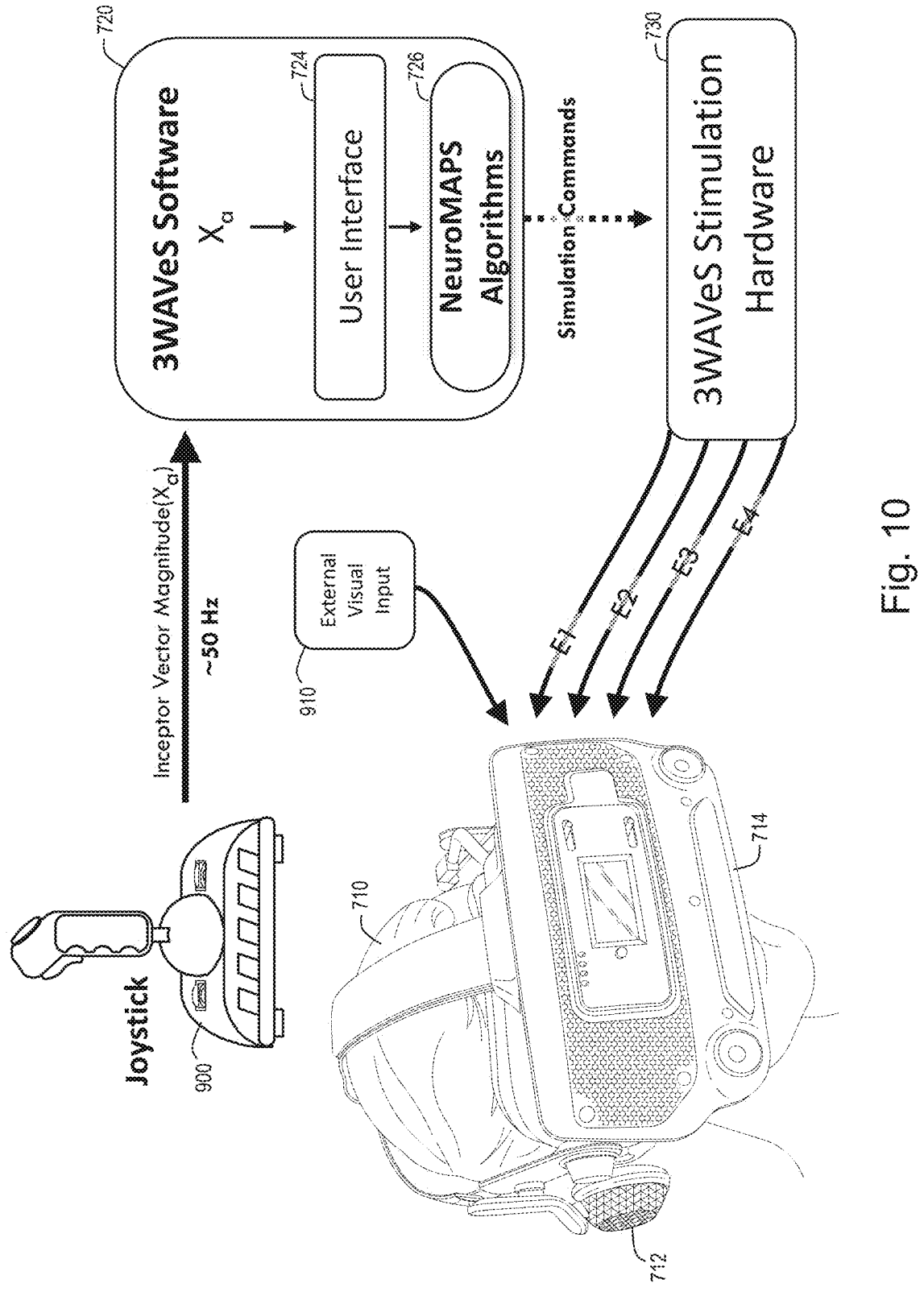
FIG. 10 shows an example embodiment of an inceptor-linked 3WAVeS system using external visual data and inceptor vector magnitude data.

FIG. 10 shows an example embodiment of an inceptor-linked operational mode of the 3WAVeS system. An inceptor device 900, here a moveable device like a joystick that can be moved with a hand, one or more fingers, etc., is operated to move to different positions in 3D space and generates magnitude and direction stimulation data $X_a$ for each of the pitch, yaw, and roll axes for each position the interceptor is moved to. The processing by the 3WAVeS software 720 and the 3WAVeS stimulation hardware 730 of the stimulation data $X_a$ is similar to the processing described for FIG. 7.

The 3WAVeS system may also be used to generate "illusory" vestibular signals in a simulated environment. For example, in low-visibility flight environments, the human vestibular system can produce erroneous sensations, often leading to loss of aircraft control and accidents. 3WAVeS may be used to simulate these erroneous, illusory signals. An illusory vestibular signal operational mode is valuable as a training tool for aircrew that likely will encounter disorienting environments in which perceived vestibular signals do not match visual signals. This type of disorientation is due to the physiologic vestibular adaptation process and continues to be a leading cause of accidents in both military and general aviation.

Figure 11:
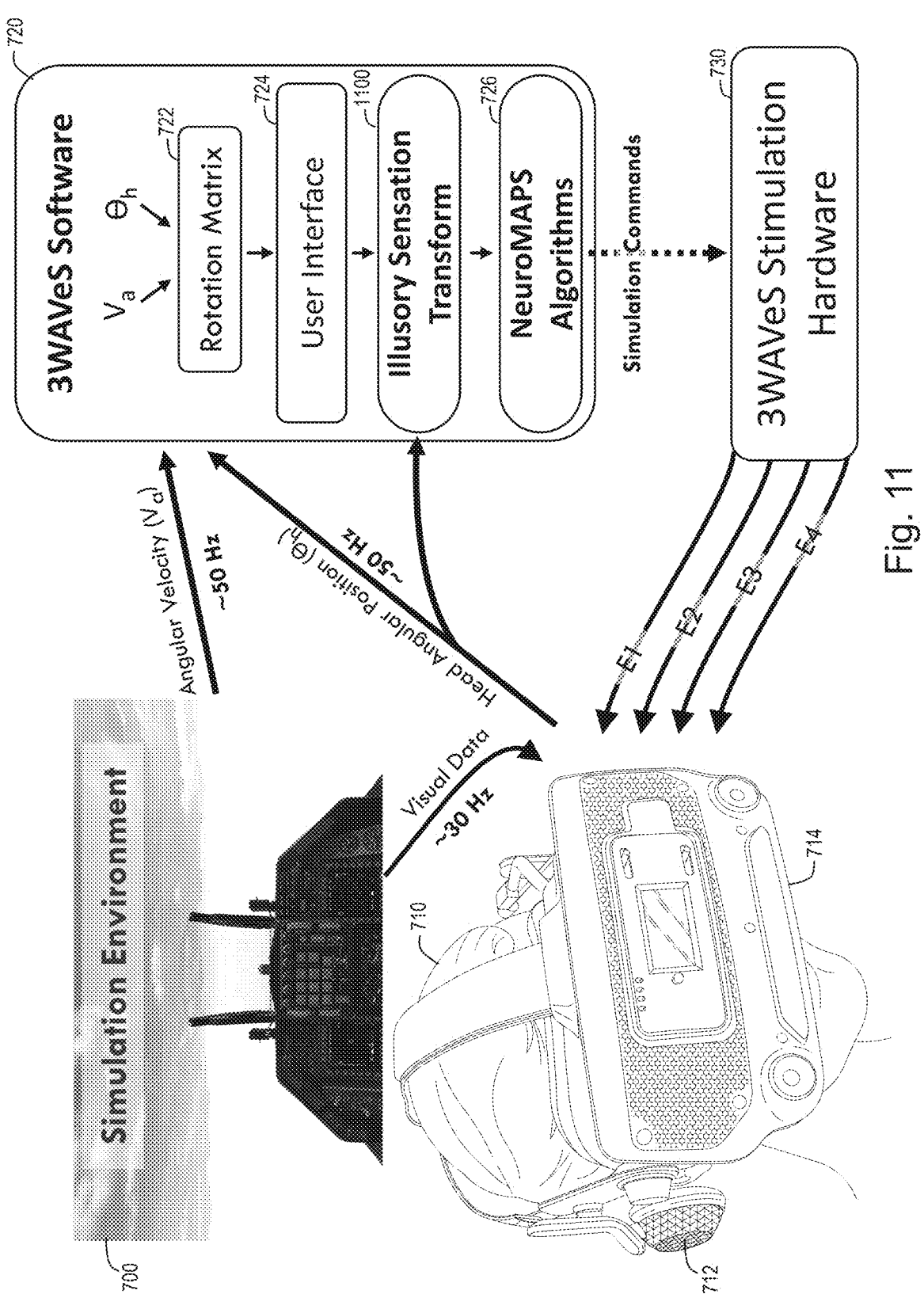
FIG. 11 shows an example embodiment of a 3WAVeS system using a simulation environment to provide visual data to a user and which performs additional illusory sensation transform processing to provide a spatial disorientation simulator.

FIG. 11 shows an example embodiment of a 3WAVeS simulator system for a spatial disorientation operational mode that uses illusory vestibular signals. The system is configured similarly as that in FIG. 8 with some additional processing performed by the 3WAVeS software 720. To generate an illusory vestibular signal, for example, the 3WAVeS system converts the kinematic data from the simulated environment 700 into an illusory sensation. This conversion may be accomplished using illusory sensation transform software 1100 that transforms inputs perceived pitch, yaw, and roll data as modified by the user interface 724. The illusory sensation transform software 1100 may be based on an analytical model of how the human vestibular system gradually adapts to a constant angular velocity. In one example embodiment, the analytical model is based on a proportional, integrative, and derivative (PID) control system with variable weights, which can be adjusted in the user interface 724. The illusory sensation transform software 1100 uses a time-history of motion (kinematic) input signals and head angular position to accurately predict how a human vestibular system would react in real life, i.e., how a human would experience real-time vestibular sensations in a spatially-disorienting scenario. The illusory sensation transform software 1100 generates transformed axial motion (kinematic) sensations modeled on head position and axial kinematic temporal history to output the axial stimulation direction and magnitude information provided for processing by the NeuroMAPS algorithms software 726.

FIG. 12 shows an example embodiment of a flow process diagram for operation of an example 3WAVeS system. Note that various modes of operation may either incorporate slightly different inputs and/or processes, such as in a Spatial Disorientation application, where "Illusory Sensation Transform" software 1100 (FIG. 11) would be included before the NeuroMAPS algorithms software 726.

The operations flow process in FIG. 12 begins with one or more forms of input data 1100 to the 3WAVeS Software. These include motion input data 1210 (motion data for two or three motion axes like yaw, pitch, and/or roll, e.g., likely but not exclusively manifested as angular velocity in units of degrees/sec) from a real-time simulated environment may be streamed from a simulator using the UDP transport layer, serial communication, etc., or from a pre-recorded environment, e.g., a 360 camera, smart device, from one or more .txt files, etc. Real-time angular position input data from a user's VR/MR headset 1220 (angular position for two or three axes like yaw, pitch, and/or roll, e.g., in units of degrees) may be streamed, e.g., using the UDP transport layer, serial communication, etc., from the VR/MR headset. Various operational modes may use varied combinations of input data type. For example, in a real-time simulation example, live environmental data may be paired with live position data from the VR/MR headset 1220. In a research setting, pre-recorded environmental data may be used for consistency. The electrical signal application to the electrodes attached to the user may be adjusted in real-time to the user's head position within the simulation.

The 3WAVeS Software processes the motion input data 1210 first using range select processing software 1230, which when executed, selects a maximum rate of angular velocity to align with a corresponding percentage axial stimulation thereby converting 3D angular velocity units of degrees/see to a percentage. The range select processing module 1230 scales percent current signal strength for delivery to an electrode based on a selection of maximum rate of angular velocity. For example, if the maximum rate of angular velocity is set to 1000°/s, then a 500°/s input signal would be output as 50%, a −250°/s input would be output as −25%, and a 1000°/s input would be output as 100%. The reason for range scaling is to match the usable range of stimulation with the range of perception.

The output from the range select software 1230 and the angular position input data from a user's VR/MR headset 1220 are input by Rotation Matrix software 1260 that rotates a nominal axial direction for each axis of stimulation so that it aligns with a current angular position of the user's head. For three axes, a three-axis rotation in space is necessary because the user's head position within a simulation significantly affects the desired stimulation pattern. For example, if a user enters a simulated dive while looking straight forward, the desired vestibular stimulation is in the pitch axis. However, if the user is looking over their shoulder during the same dive, the stimulation should be manifested in the roll axis. The Rotation Matrix software 1260 applies a rotational transformation to the multi-axial data stream based on input data from the VR/MR headset 1220 to rotate a nominal axial direction by the user's head angular position to generate corresponding 3D axial stimulation percentages. The spatial transformation performed by the Rotation Matrix software 1260 improves the fidelity of 3WAVeS vestibular stimulation.

Figure 13:
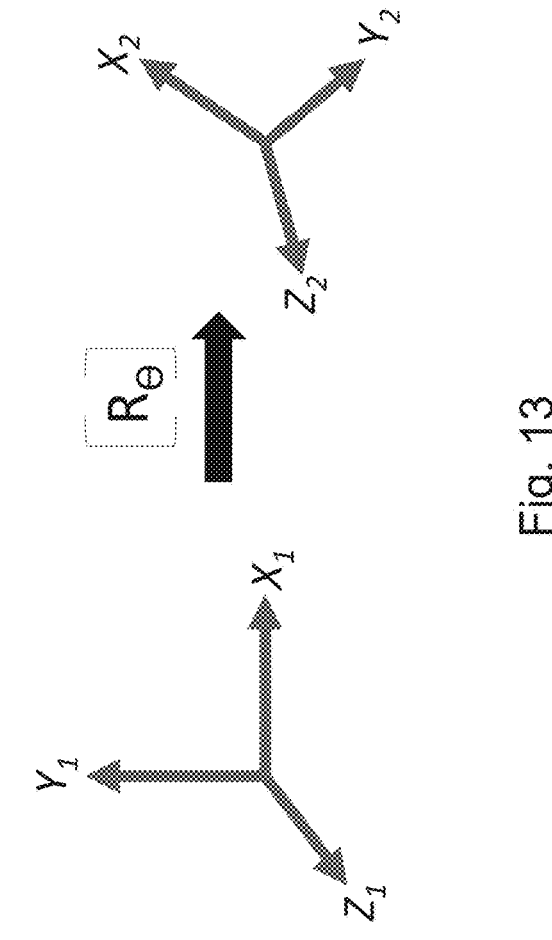
FIG. 13 illustrates an example application of a rotation matrix to system coordinates.

Regarding the rotational transformation, FIG. 13 illustrates an example application of a rotation transformation to $X_1$, $Y_1$, $Z_1$ coordinate system axes to rotate the $X_1$, $Y_1$, $Z_1$ axes by $\ominus$ degrees to a new orientation $X_2$, $Y_2$, $Z_2$. The rotation may be applied for example using known example methods such as but not limited to Euler Angles, Euler Parameters, and Quaternion.

Figure 14:
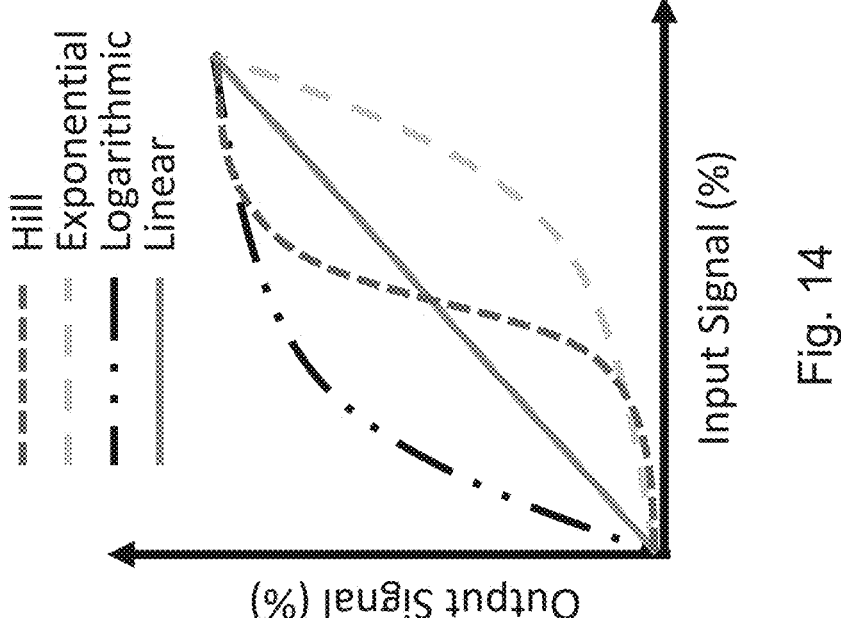
FIG. 14 is a graph showing a channel sensitivity transform for various signal onset settings.

The output from the Rotation Matrix software 1260 is a percent stimulation magnitude value for each axis, which has been modified from the input by the user's head rotation, and these axial percent stimulation magnitudes are input by channel sensitivity software 1270 for processing. Each of the axial percent stimulation magnitudes is processed using a selectable and tunable function to adjust the input percent stimulation magnitude to an output percent stimulation magnitude for the purpose of selectively adjusting an onset rate of stimulation to the user via each of the stimulation electrodes. This function allows output sensitivity of the input axial signals to be adjusted for each channel. Some example functions include, but are not limited to, (i) a linear function, where the input and output percent stimulation magnitudes are directly mapped at a 1:1 ratio, (ii) an early-onset logarithmic function or a late-onset exponential function, and (iii) a function based on a Hill type model sometimes used in biochemical and electrochemical applications. Regarding a Hill type model function, the human vestibular system may not linearly sense motion. Rather, various biologic vestibular systems function more on an "S" curve shape, where sensitivity is low at the low range, very high at mid-range, and low again at high ranges. In this case, a Hill type model function may be better suited. The outputs from the channel sensitivity software 1270 are scaled axial stimulation percentages. FIG. 14 is a graph showing four different example channel sensitivity transforms (input % to output %) that may be used to achieve various signal onset settings.

The scaled axial stimulation percentages output from the channel sensitivity software 1270 are input into stimulation peak software 1280 which converts the axial stimulation percentages into a corresponding electrical stimulation current value (e.g., in mA) based on selection of a maximum current value. In other words, the resulting currents are typically less than and never greater than the maximum current value (assuming normal operation). Example default current values, for user comfort, may be 1.25 mA in each axis selectable up to 2.5 mA maximum current. These example default values may be modified, and other values may be used depending on the application.

Output from the stimulation peak software 1280 is input into the Neurologic Multi-Axis Paradigm for Stimulation (NeuroMAPS) software 1290. The specific NeuroMAPS algorithm to be utilized in converting calculated axial stimulations into current polarity and magnitude for each electrode in the system is dependent upon multiple factors including the type of input data, the desired use case, and number of electrodes in the system, but can be selected and adjusted within the user interface. A set of example Neuro-MAPS algorithms for multiple cases of varied input data can be seen in FIG. 15. Detailed functionality of NeuroMAPS algorithms are later described, but in general, analytical circuit modeling and electrophysiology techniques may be used to convert desired stimulations along two or more axes into polarity and magnitude values for each electrode within the system, resulting in an accurate neuro-vestibular sensation while avoiding formation of conflicting current gradients that would cause undesirable sensation. Ultimately, the NeuroMAPS software uses the 2 or 3 axial electrical stimulation current values input to generate 4 electrode digital commands in the example where 4 electrodes are used. The digital commands are sent, e.g., via a peripheral or serial interface (e.g., USB, RS232, Bluetooth, etc.), to the 3WAVeS Hardware system 1250.

The 3WAVeS hardware 1250 is described in detail later; however, a brief description is provided here. The 3WAVeS hardware 1250 includes multiple, e.g., two to eight, independent bidirectional current sources and a relay in series with each current source. In an example embodiment, four independent bidirectional current sources may be used allowing full multi-axis vestibular interfacing control. The number of independent bidirectional current sources is not limited to 2-8. The 3WAVeS hardware 1250 receives the input commands from the NeuroMAPS software 1290, via a serial or peripheral interface, with each input command having real-time instructions for operating each current source and associated relay. Each command includes relay activation status information for each current source relay and electrical current amplitude information for each of the independent current sources. When the current sources are connected as an output via properly chosen and placed electrodes, the desired vestibular sensation is induced in an end user. The 3WAVeS hardware 1250 can execute each and any of the NeuroMAPS stimulation paradigms in order to generate accurate sensations of vestibular motion including those situations noted above for the known vestibular motion stimulation system that resulted in fundamental errors because undesired electrical gradients were generated, negating or even reversing desired stimulations. The NeuroMAPS vestibular stimulation mapping paradigms can transform all combinations of one, two, three, or more concurrent input axial signals into electrical outputs which are appropriately interpreted as sensations of motion by the user's vestibular system.

Figure 15:
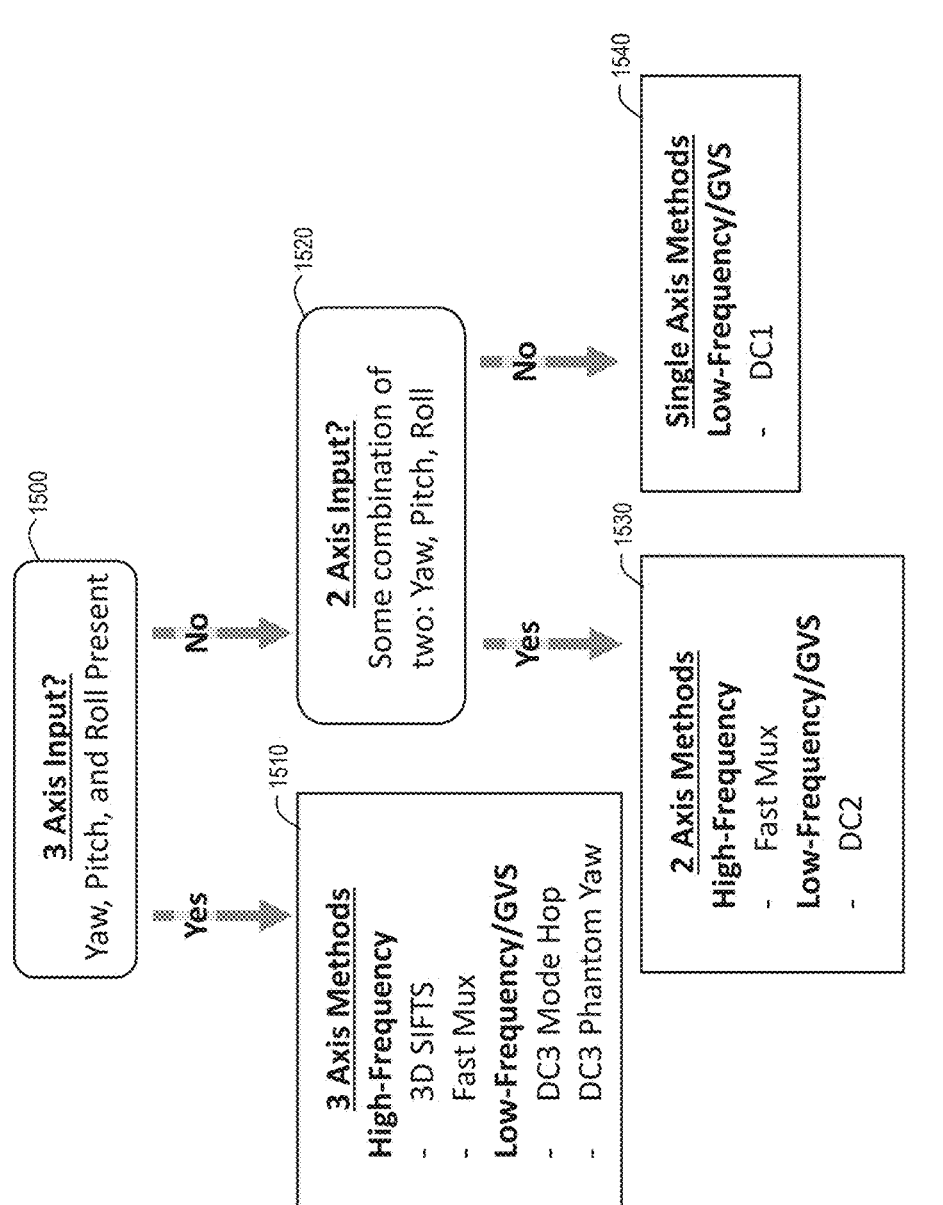
FIG. 15 is an example embodiment of a process to select from a set of Neurologic Multi-Axis Paradigms for Stimulation (NeuroMAPS) algorithms based on inputs from one or more axes (axial inputs)

FIG. 15 is an example embodiment of a process to select automatically or manually by a user one or more algorithms from the set of Neurologic Multi-Axis Paradigms for Stimulation (NeuroMAPS) algorithms for processing the motion input axial data based on the number of concurrent axial inputs. This selection process can occur in real time, and the 3WAVeS hardware permits switching between the stimulation paradigms in real time. Although some of the low-frequency paradigms, like single channel low-frequency/GVS (DC1), may be implemented using known vestibular stimulation hardware, it is the 3WAVeS hardware 1250 that can correctly run the more complex high-frequency and multi-channel paradigms, like DC2, DC3, 3D SIFTS and Fast Mux, to provide improved, multi-axis vestibular sensation. An overview of example high and low frequency stimulation paradigms or methods is provided below followed by more detailed explanations of the individual stimulation paradigms contained within each set.

The inventors recognized that a solution to the conflicting electrical gradients formed by some multi-axis stimulations in known systems is to split the stimulations into a "duty cycle" or "pulse-width modulated" format in which each stimulation channel or set of stimulation channels is stimulated for a percentage of the total stimulation time. The inventors also realized that generating these pulse-width modulated stimulations at a higher frequency than 20 KHz frequency avoids generating audible signals. Thus, the term "high frequency" in this context means that if it is desirable to avoid generating audible signals, which may or may not be the case for a particular application, then the signal frequency is above the audible range for humans. However, the pulse-width modulated signals described for high-frequency paradigms may be generated at lower frequencies below the audible range if desired.

Example embodiments described below include two pulse-width modulation paradigms which utilize the proclivity of the human neural system in interpolating rapid inputs. Specifically, these paradigms utilize the concept of pulse-width modulation to allow the relevant channels to stimulate only a fraction of the total "on" time of stimulation, and by repeating the modulated stimulations quickly enough, the human neural system is unable to discern that these stimulations are not occurring full time. The two example pulse-width modulation paradigms are referred to as "Fast Multiplex" and 3-Dimensional SuperImposed Fast Transcranial Stimulation (3D SIFTS).

The Fast Multiplex paradigm splits all independent axes into individual time-separated stimulation segments (e.g., 33% pulse width each of three axes). The 3D SIFTS paradigm combines two of the axes with some modifications to ensure aberrant gradients do not form (e.g., 50% pulse width for two axes out of three axes). Although Fast Multiplex offers more individual channel control due to the discretized nature, the lower percentage pulse width stimulations, e.g., 33% pulse width stimulations, mean that less energy is transferred in a given stimulation than with 3D SIFTS, which delivers a higher percentage, e.g., 50% pulse width simulations.

Referring again to FIG. 15, step 1500 determines whether the motion input data includes input data for 3 axes, e.g., yaw, pitch, and roll. If so, one of three axis NeuroMAPS stimulation algorithms may be selected in 1510 from 3D SIFTS, Fast Mux, and less accurate simulation known methods referred to as Low-Frequency Galvanic Vestibular Stimulation (GVS) with examples identified as DC3 mode hop and DC3 phantom yaw. If not, then step 1520 determines the motion input data includes input data for 2 axes, e.g., yaw and pitch, yaw and roll, and pitch and roll. If so, then one of the two axis NeuroMAPS stimulation algorithms, including Fast Mux and Low-Frequency GVS (e.g., DC2 described below), may be selected in step 1530. Otherwise, step 1420 determines the motion input data includes input for one axis, and step 1540 selects the Low-Frequency GVS stimulation algorithm (e.g., DC1 described below).

Figure 16:
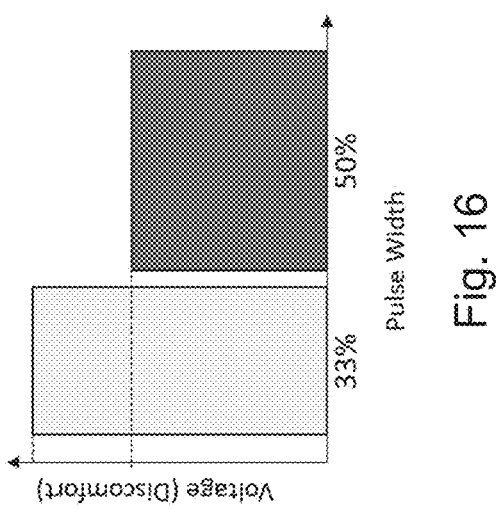
FIG. 16 is a graph showing a relationship of voltage to pulse width for constant energy injection.

FIG. 16 is a graph showing a relationship of stimulation voltage to pulse width for constant energy injection. As the voltage increases, discomfort experienced by a user typically increases. More voltage is needed for a 33% pulse width stimulation as compared to a 50% pulse width stimulation. Stated differently, the 50% pulse width stimulation reduces the magnitude of voltage needed during a given stimulation to inject the same amount of electrical energy as compared to the magnitude needed for 33% pulse width stimulation.

For the Fast Mux neural stimulation, stimulation time is split into equal portions relative to the number of channels to be stimulated, with a stimulation time fraction per channel equal to 1/n, where n equals the number of stimulation channels. In the case of vestibular interfacing applications, three channels are the most common but not required. In three channel applications, each channel operates with a 33% pulse width with each third representing the time during which each channel can stimulate as illustrated in the three graphs shown in FIG. 16 for roll, pitch, and yaw current stimulation channels. As mentioned above, to avoid perception of the channel switching and auditory effects, the stimulation may be generated at higher frequency, e.g., approximately 20 kHz-100 kHz. Fast Mux takes advantage of the human neural system's inability to distinguish rapidly oscillating inputs from constant ones, which is an effect similar to watching a movie, where a series of individual frames appears to the eye as a continuously moving image.

Figure 17:
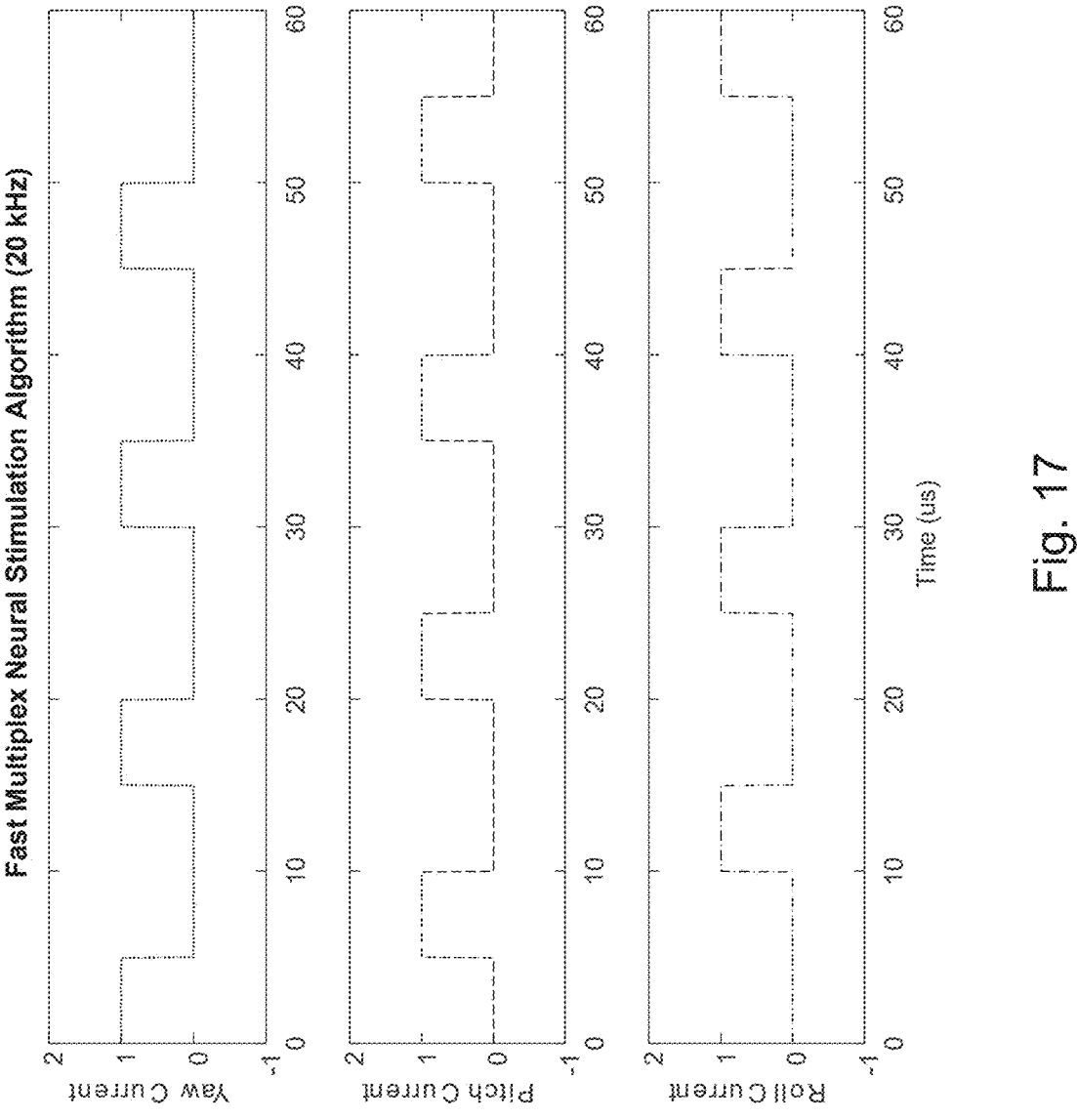
FIG. 17 is a graph of discretized pulse width stimulations in each channel with an example embodiment of a Fast Multiplex neural stimulation method.

FIG. 17 shows an example of 20 kHz Fast Mux signal generation. Each stimulation channel is "on" for 5 μs, and "off" for 10 μs. This sequence repeats every 15 μs, leading to a 33% pulse width for each channel, with no concurrent stimulation. Fast Mux stimulation may be desired in applications where all stimulation channels would conflict with each other during concurrent stimulations or in other situations in which concurrent stimulation is not possible. The yaw current signal, the pitch current signal, and the roll current signal do not substantially overlap in time, e.g., in a range of zero overlap up to about 10% possible overlap.

3D SIFTS also operates on the principle of breaking stimulation time into segments but combines stimulations of two or more non-competitive stimulation channels. In the three-dimensional neural interfacing application, 3D SIFTS is advantageous because it increases the energy able to be transmitted through each channel per stimulation cycle (see FIG. 15) by decreasing the number of pulse divisions from three to two, which increases the pulse width from 33% to 50%. This reduces the amount of voltage needed during a given stimulation to inject the same amount of electrical energy.

Figure 18:
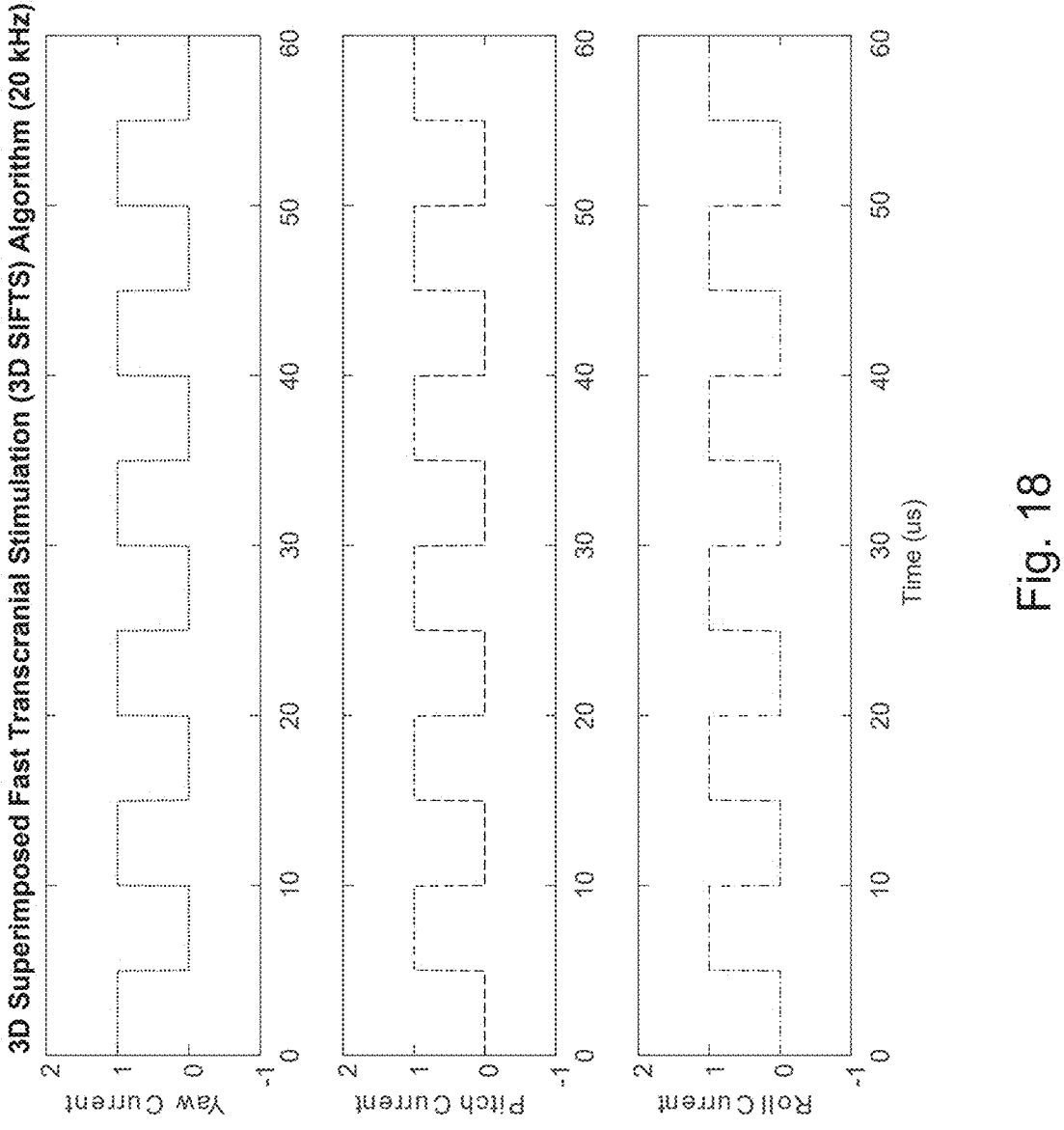
FIG. 18 is a graph of partially-combined pulse width stimulations in each channel with an example embodiment of a 3-Dimensional SuperImposed Fast Transcranial Stimulation (3D SIFTS) method.

FIG. 18 show graphs of partially combined pulse width stimulations in each channel with an example embodiment of a 20 kHz 3D SIFTS process. In this example, the pitch and roll axes are concurrently stimulated at substantially the same time, while the yaw axis is stimulated on the other portion of the 50% pulse width cycle. More generally, two signals of the yaw current signal, the pitch current signal, and the roll current signal have the same or similar time-multiplexed modulated signals that at least substantially overlap in time, e.g., overlap by about 90-100%, and the other signal of the yaw current signal, the pitch current signal, and the roll current signal does not substantially overlap the two signals in time, e.g., in a range of zero overlap up to about 10% possible overlap.

Figure 19:
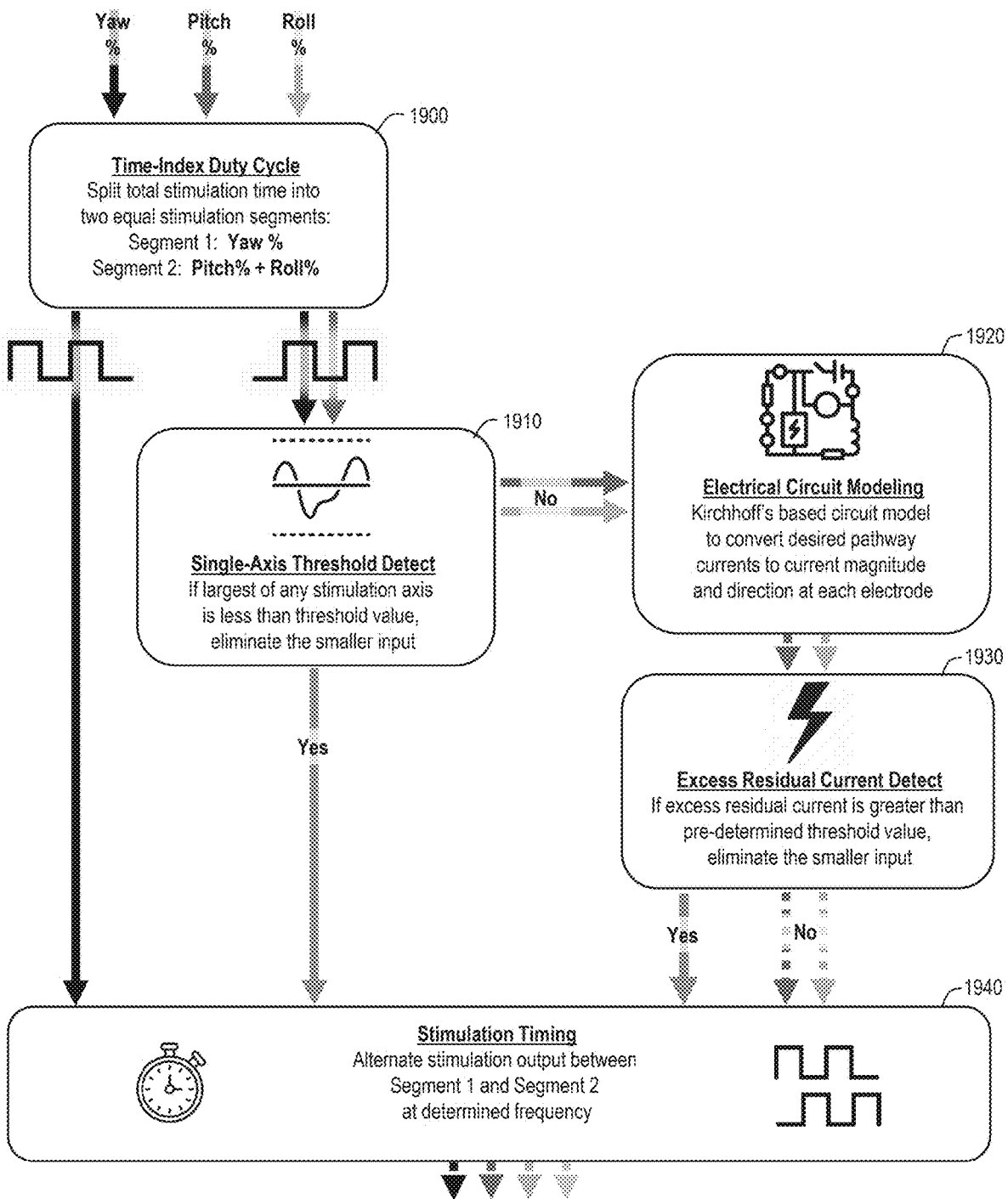
FIG. 19 is a flow diagram illustrating an example embodiment of a 3D SIFTS signal processing method.

The combinatorial nature of 3D SIFTS requires that various processes and transforms be applied to convert the input signal to meaningful electrical outputs. FIG. 19 is a flow process diagram illustrating an example embodiment of a 3D SIFTS signal processing method. In time-index duty cycle process 1900, yaw, pitch, and roll percentage stimulation inputs are received, and a time index duty cycle is determined. The total stimulation time is split into two equal stimulation segments where segment 1 is for yaw stimulation and segment 2 is for combined pitch and roll stimulation. As another example, pitch and yaw can be paired together because oftentimes yaw and roll strongly interfere with each other. Segment 1 is provided to stimulation timing process 1940. Segment 2 is processed in single-axis threshold detect process 1910 to determine if the largest stimulation magnitude or percentage between the pitch and roll is below a single axis threshold value. If so, the smaller magnitude or percentage of the segment 2 stimulations is eliminated and the larger magnitude or percentage of the segment 2 stimulations is provided to stimulation timing process 1940. If the largest stimulation magnitude or percentage between the pitch and roll is equal or above a single axis threshold value, then the segment 2 stimulations are provided to electrical circuit modeling process 1920. For example, Kirchhoff's circuit modelling is used to convert each desired channel current to a current magnitude and direction (a vector) at each electrode (described further below). Excess residual current detect process 1830 determines whether the residual current calculated by step 1920 electrical circuit modeling exceeds a pre-determined threshold. If so, then the smaller magnitude or percentage of the segment 2 stimulations is eliminated, and the larger magnitude or percentage of the segment 2 stimulations is provided to stimulation timing process 1940. This residual cutoff resolves the tendency of residual currents to be generated in proportion to the magnitude imbalance between the pitch and roll stimulation channels. If the largest stimulation magnitude or percentage between the pitch and roll is equal or above a single axis threshold value, then the segment 2 stimulations are provided to stimulation timing process 1940. Stimulation timing process 1940 controls the stimulation timing by alternating the stimulation output between segment 1 and segment 2 stimulations at the determined duty cycle and frequency.

Figure 20:
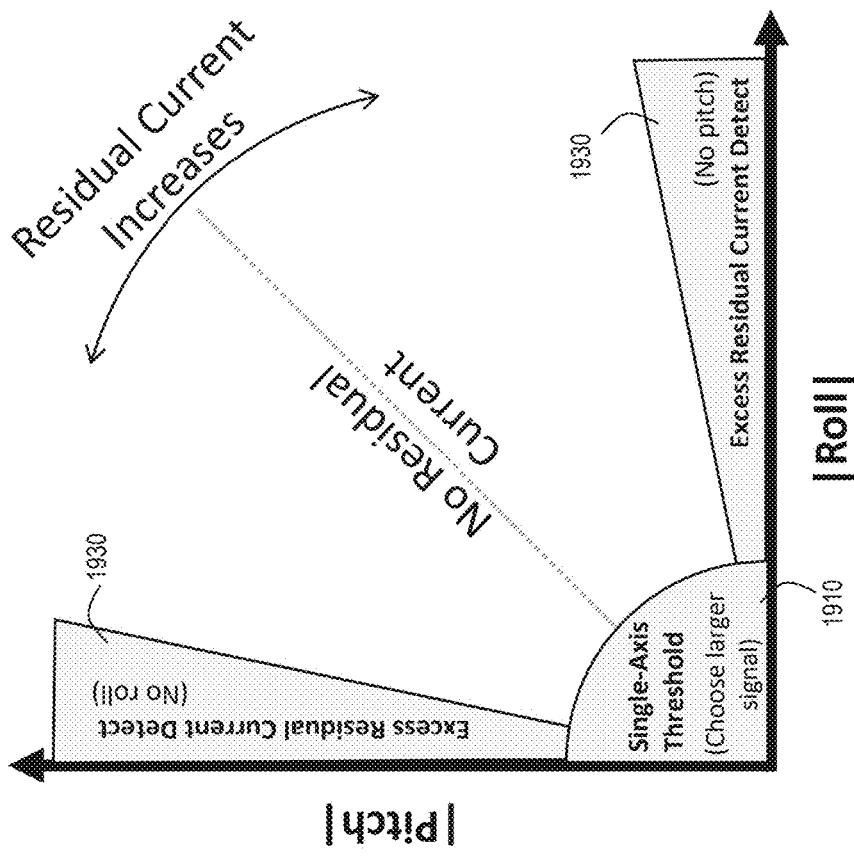
FIG. 20 is a graph showing examples of excess residual pitch current and excess residual roll current.

FIG. 20 is a graph visually demonstrating the operation of Single Axis Threshold process 1910 and Excess Residual Current Detect process 1930. If the magnitude of both pitch and roll fall below the radius of the Single-Axis threshold 1910, only the larger signal is chosen and preserved. If after this point the magnitude of pitch and roll are not equal, then some residual current is formed that could cause discomfort to the user wearing the electrodes. If the imbalance becomes excessive, then the Excess Residual Current Detect block 1930 chooses and preserves only the larger of the two signals.

Electrical circuit modeling process 1920 in FIG. 19 accurately generates signals in both axes of the paired stimulation time segment 2. For example, the pairing choice of pitch and roll leads to four possible stimulation input combinations in the paired-channel stimulation cycle, as seen in Table 3 below. This example circuit modeling designates one electrode as primary, and two others as secondary, with one electrode always being required to be removed for proper gradient control. The input columns for pitch and roll designate forward (F), left (L), right (R), and back (B).

TABLE 3

| | | Electrode Selection | | |
| --- | --- | --- | --- | --- |
| Input | | Primary | Secondary | Secondary |
| Pitch | Roll | Electrode | Pitch Elec | Roll Elec |
| F | L | 2 | 1 | 4 |
| F | R | 3 | | |
| B | L | 3 | | |
| B | R | 2 | | |

The "Electrode Selection" portion of Table 3 shows which electrode is designated as "Primary" depending on the input. Due to the electrical gradients that form during multi-channel physio-electric stimulations, the current across both concurrent stimulation pathways are the same direction relative to the Primary Electrode (e.g., both towards or both away from) as illustrated for all four input combinations in FIG. 21.

Figure 21:
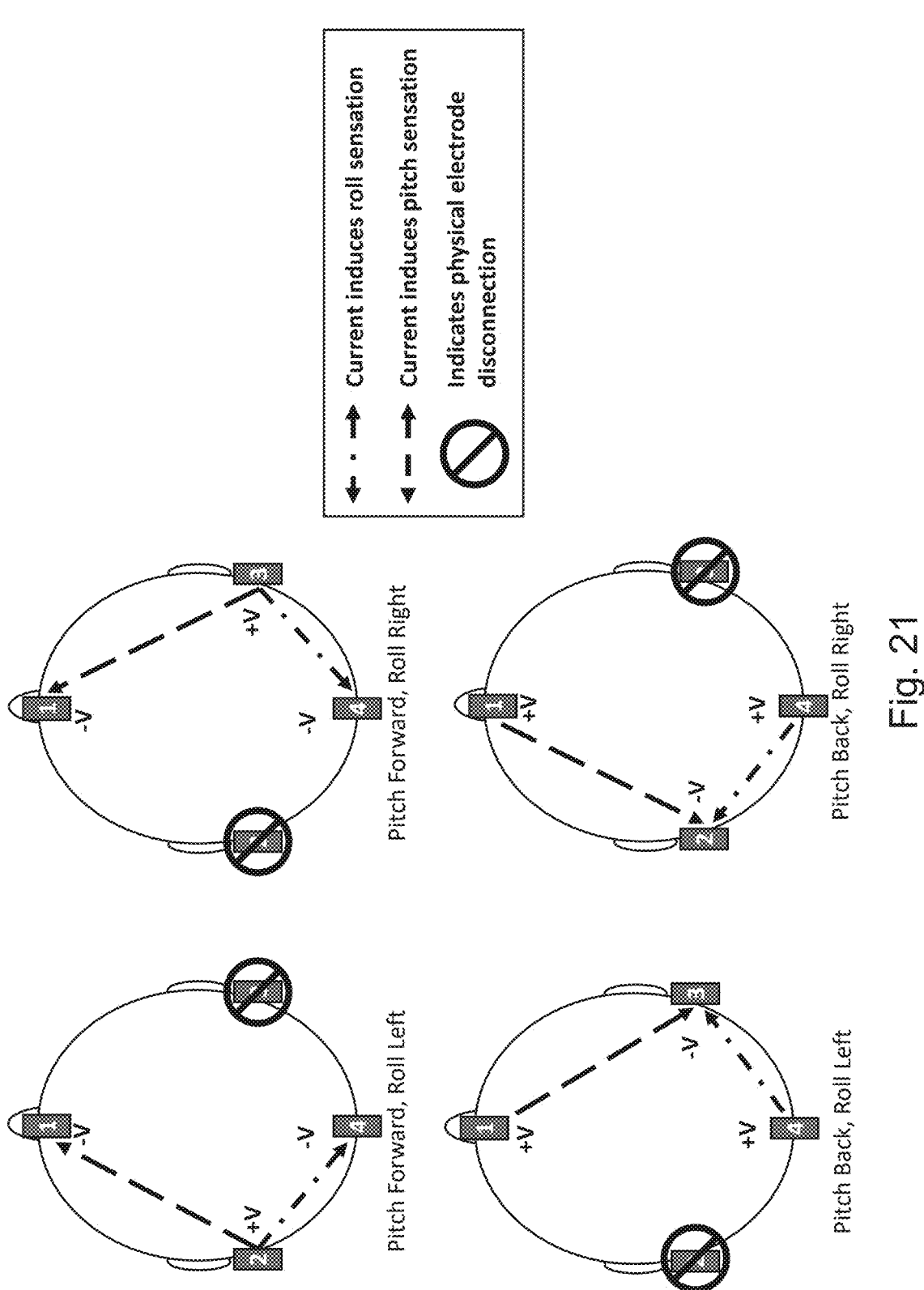
FIG. 21 shows example input combinations and relative direction of current transmission in 3D SIFTS concurrent channel stimulation.

FIG. 21 shows example input combinations and relative direction of current transmission in 3D SIFTS concurrent channel stimulation. Because of the gradients that form, one secondary electrode is physically disconnected from the physiologic circuit in the 3D SIFTS stimulation. As described below, the secondary electrode disconnection is automatically accomplished via relays in the 3WAVeS hardware and is indicated for the four input combinations in FIG. 21 using a cross out symbol.

The inventors developed a series of equations based on the selected electrode arrangement which controls stimulation pathway currents during the concurrent stimulation cycle. Stimulation pathway currents are like the currents shown in FIG. 21 moving from one electrode to another electrode. For example, two stimulation pathway currents are shown in the pitch forward, roll left diagram in FIG. 21. These equations describe the electrical circuit model needed to calculate current sinking and sourcing at each electrode in the system based on a desired roll and pitch current, within the concurrent stim cycle (pitch+roll). They convert the desired current across each stimulation pathway into the necessary commands for each of the four electrodes used in the example application. In particular, with three channels and four electrodes, the following equations are used:

$$Ires(Iroll, Ipitch) = \frac{Iroll * Rroll - Ipitch * Rpitch}{Rres}$$

$$Ipitch_s = Ires - Ipitch$$

$$Iprimary - Ipitch + Iroll$$

$$Iroll_s = -Iroll - Ires$$

where $R_x$ = pathway impedance, and $Ires$ = residual current

Iroll and Ipitch are the input to the function. The sign and magnitude of each of Iroll and Ipitch dictate the desired direction and amplitude of current to be injected across each stimulation current pathway. The sign of each signal component is used to digitally assign the primary electrode as per Table 3 and FIG. 21. After the electrical circuit modeling process 1920 of FIG. 19 is completed, another check for excess residual current is performed. If an adjustable threshold is exceeded, the lower-magnitude signal is either adjusted or eliminated in excess residual current detect process 1930 to reduce the magnitude of the residual current. In stimulation timing process 1940, the output from the paired stimulation channel is time-multiplexed with the output of the single axis stimulation channel, and the signals are alternated at high frequency over the relevant set of electrodes.

Figure 22:
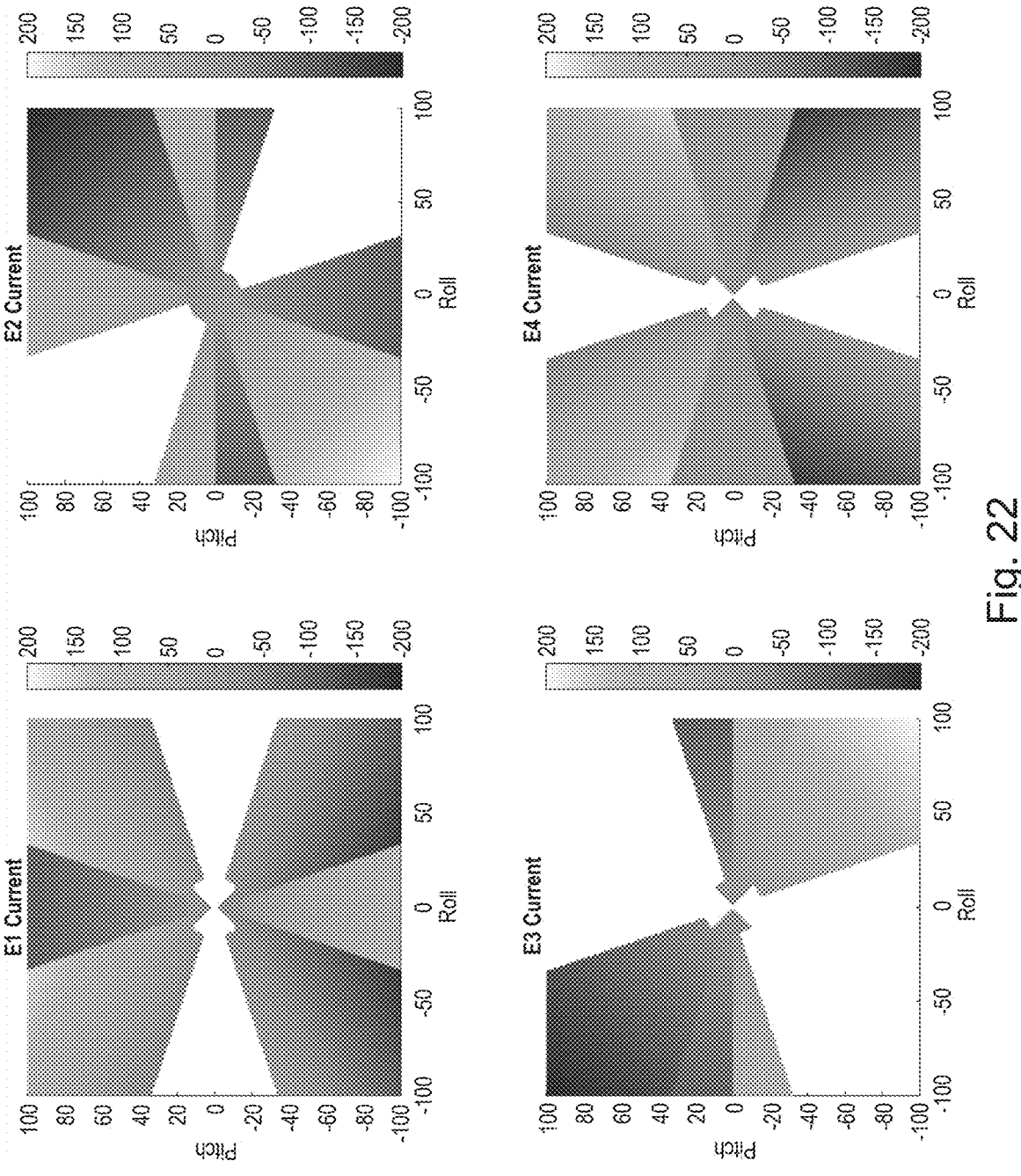
FIG. 22 are example graphs of example current outputs at each of four electrodes E1-E4 in a roll and pitch paired stimulation segment.

FIG. 22 shows four graphs illustrating the calculated electrode current outputs at all four electrodes (E1-E4) in the paired Pitch and Roll stimulation time segment example with an example 15% minimum threshold cutoff and a 2× lower amplitude channel residual cutoff.

Even though galvanic vestibular stimulation, an example low frequency method, does not provide complete, multi-axis stimulation control, it still may be useful in certain neurologic interfacing scenarios. Low frequency paradigms convert up to three axial inputs into a maximum of two concurrent stimulations across vestibular pathways (defined according to FIG. 3) which do not result in aberrant electrical gradients across the user electrodes. The low frequency methods are labeled as DC "X", where the DC stands for Direct Current, and the "X" indicates the number of dimensional inputs.

DC1 is analogous to the galvanic vestibular stimulation algorithm but only permits processing of one input axis at a time. A single axial input is directly mapped to the desired electrode pair pathway according to FIG. 3.

A DC2 stimulation algorithm uses the same methods as 3D SIFTS, except that no high-frequency timing element is utilized. Instead, the paired, two-channel, full-time stimulation is employed. Thus, the "single axis threshold," "electrical circuit modeling," and "excess residual current detect" processes in FIG. 19 are used.

A DC3 stimulation algorithm is an extension of the DC2 stimulation algorithm in which all three rotational axes are input and may be accomplished in multiple manners. In one example, any yaw signal magnitude is summed to the roll axis. For example, if a +50% yaw magnitude sensation is calculated, a +50% roll magnitude would instead be simulated. This substitute stimulation is believed to be perceived similarly by the user due to similar perception in the yaw and roll axes. If varied magnitudes of yaw and roll are needed for stimulation, various techniques of summing or comparing the individual signals to a net roll output may be used including, for example, direct vector addition, sum-squared addition, or other.

Another version of the DC3 algorithm is called channel hopping, where the channel hopping algorithm, when executed, compares the magnitudes of the desired yaw vs pitch+roll signals, and automatically selects the stimulation mode in real-time, allowing a synthesized three-axis stimulation. Multiple calculation modes can be employed to allow the system to properly choose the stimulation mode in real time.

FIG. 23 shows an example embodiment of a 3WAVeS graphical user interface where a user may interact with the 3WAVeS system to control operational parameters and see current activity of the 3WAVeS system. Example operational parameters include input and output settings, user settings, movement inputs, user profile loading and saving, stimulation sensitivities and intensities (see electrode currents), immediate stimulation feedback (such a perceived angular velocities shown), and time history of stimulations (see the graphs of stimulations over time). The user interface contains a range of submenus and feature lists that together allow significant customization of the stimulation to each user.

Figure 24:
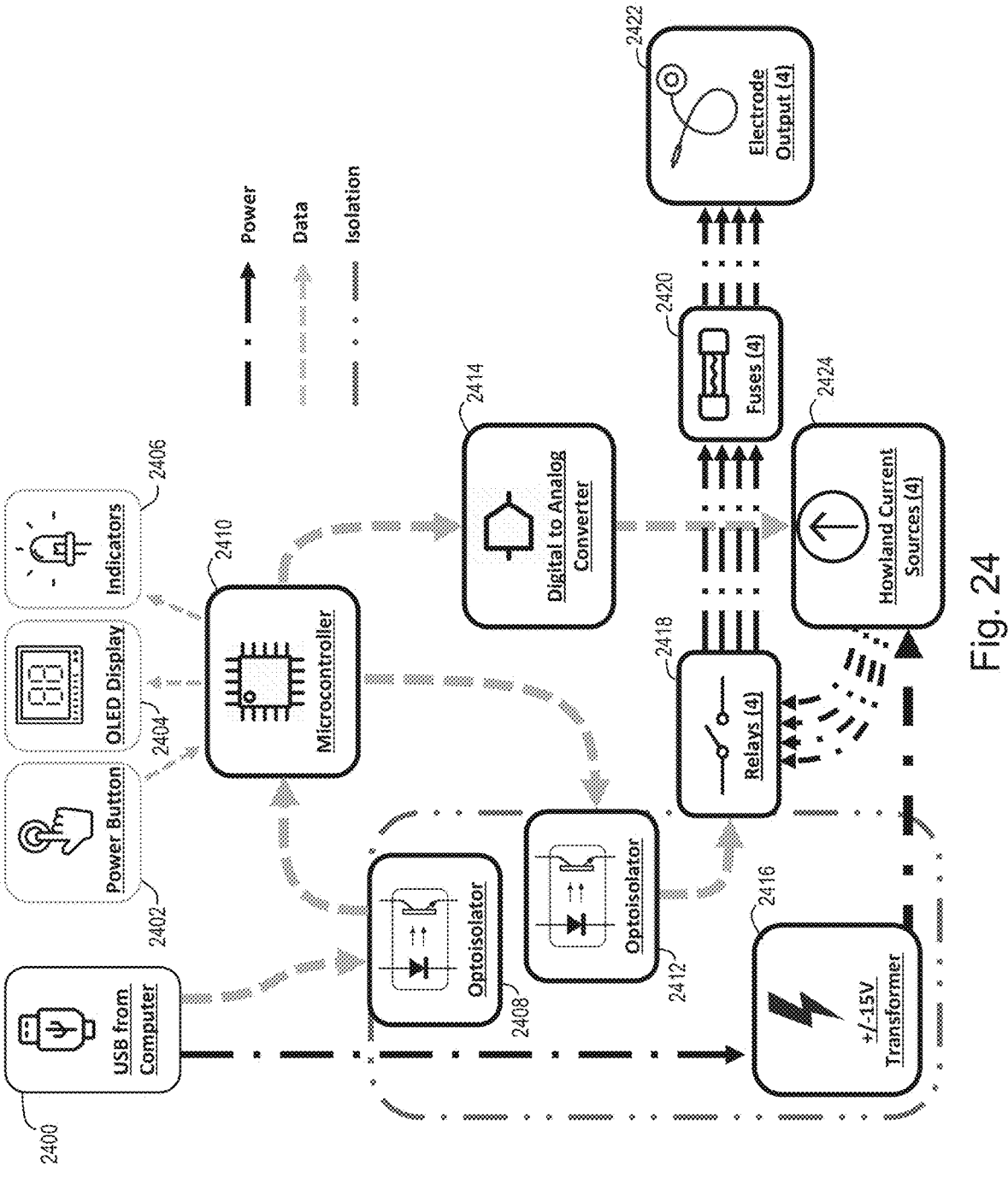
FIG. 24 shows an example embodiment of a hardware diagram for a 3WAVeS system.

FIG. 24 shows an example embodiment of a hardware diagram for a 3WAVeS system. In one example implementation, the 3WAVeS hardware may be implemented on a single chip, but this is not required. One or more microcontrollers 2410 control and coordinate the operation of the various hardware components shown in FIG. 24 and interface, via the peripheral or serial interface shown here as a USB interface 2400, with communications from the NeuroMAPS software 1290 including receiving the electrode output commands. Stimulation control commands (digital instruction) are sent by the NeuroMAPS software 1290 over a data port in the USB interface 2400. Other data ports such as Serial, COM, or wireless data ports may be used.

The USB interface 2400 also provides power for the 3WAVeS hardware. However, power may also be provided by battery and/or wirelessly.

In example embodiments, power isolation hardware is provided to protect and isolate various components from power surges, spikes, etc. The power isolation hardware includes a transformer 2416 to convert DC power from the USB 2400, typically at 5 volts, to +/−15 volts which is used to drive the current sources 2424. The isolation hardware includes an optoisolator 2408 to isolate the data communications from the NeuroMAPS software 1290 to the microcontroller 2410. An optoisolator 2412 isolates operational control signals from the microcontroller 2410 that operate (open or close) the relays 2418.

Four independent current sources 2424 are controlled by analog electrode signals output by a digital to analog converter 2414 based on the digital input commands from the selected NeuroMAPS algorithm and provided by the microcontroller 2410. The current sources 2404 then deliver precise stimulation currents delivered to each electrode 2422 via a corresponding protective fuse 2420. There is a one-to-one correspondence between current sources and electrodes. Fewer or more electrodes would be matched with fewer or more current sources. In example embodiments, each of the independent current sources 2404 may include a modified Howland circuit, which uses feedback layers to ensure that the desired current output is accurately and safely generated.

In example embodiments, the 3WAVeS hardware system may be IEC 60601-1 compliant because the optical isolators

2408 and 2412 physically separate the voltages used to operate the microcontroller 2410 from the current sources 2424 used to generate electrical stimulations. This design significantly improves safety by reducing the opportunity for stray carryover voltages. The fuses 2420 may for example be micro 5 mA fuses that are physically destroyed if current reaches or exceeds the level of 10 mA, ensuring that the user is not subjected to overcurrent.

The microcontroller 2410 operationally controls the relays 2418 to automatically disconnect a corresponding electrode based on the electrode output commands from the NeuroMAPS software 1290 when the stimulation scenario requires that one or more electrodes be disconnected. Frequency generation for a high-frequency clock for operating high frequency NeuroMAPS methods is provided by the microcontroller 2410. A power button 2302 is connected to the microcontroller 2310, and various indicators 2306 (e.g., lights, sounds, etc.) and an optional secondary display screen 2304 allow a user to see various information about the 3WAVeS system in real time.

Figure 25:
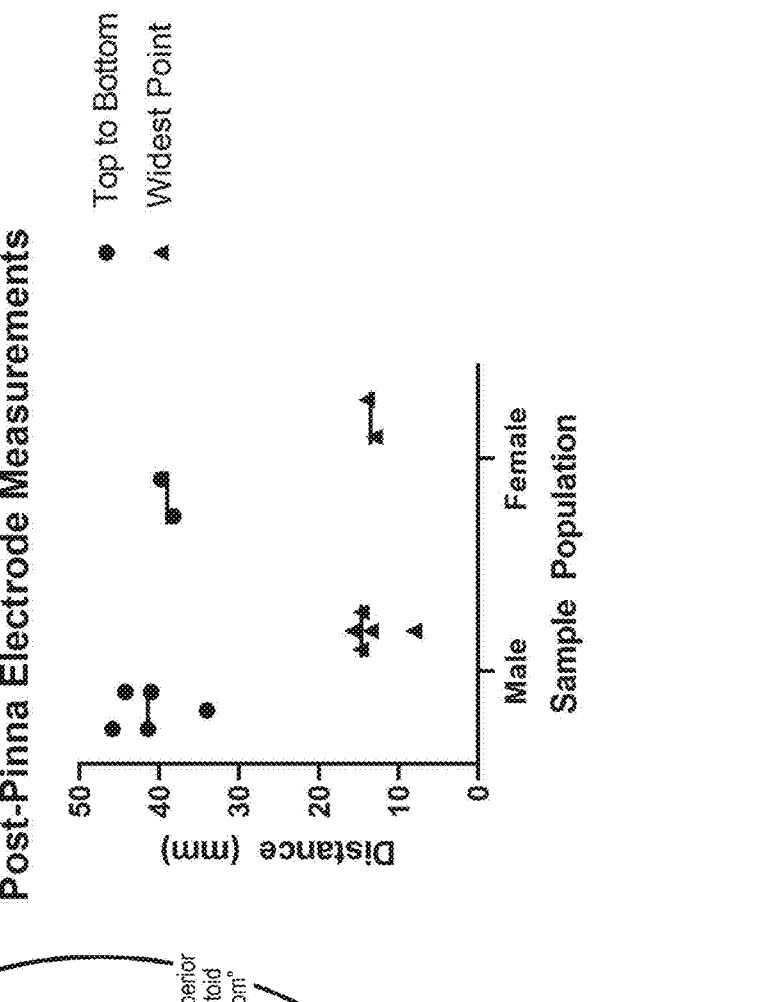
FIG. 25 shows measurements taken for design of mastoid electrodes in accordance with example embodiments with data results from these measurements.

Example embodiments provide custom electrodes for epidermal stimulation over the mastoid process that make maximal contact with the hair-free area immediately behind the ear which is a bilateral stimulation location for vestibular stimulation. FIG. 25 shows measurements taken for the design of mastoid electrodes in accordance with example embodiments with data results from these measurements of the hair-free area behind the ear collected on seven adult subjects, n=5 men, and n=2 women. Two measurements were collected—the "Widest Point" and the "Top to Bottom" as illustrated on the left side of the figure. The measurement results are shown on the right side of the figure.

Figures 26, 27:
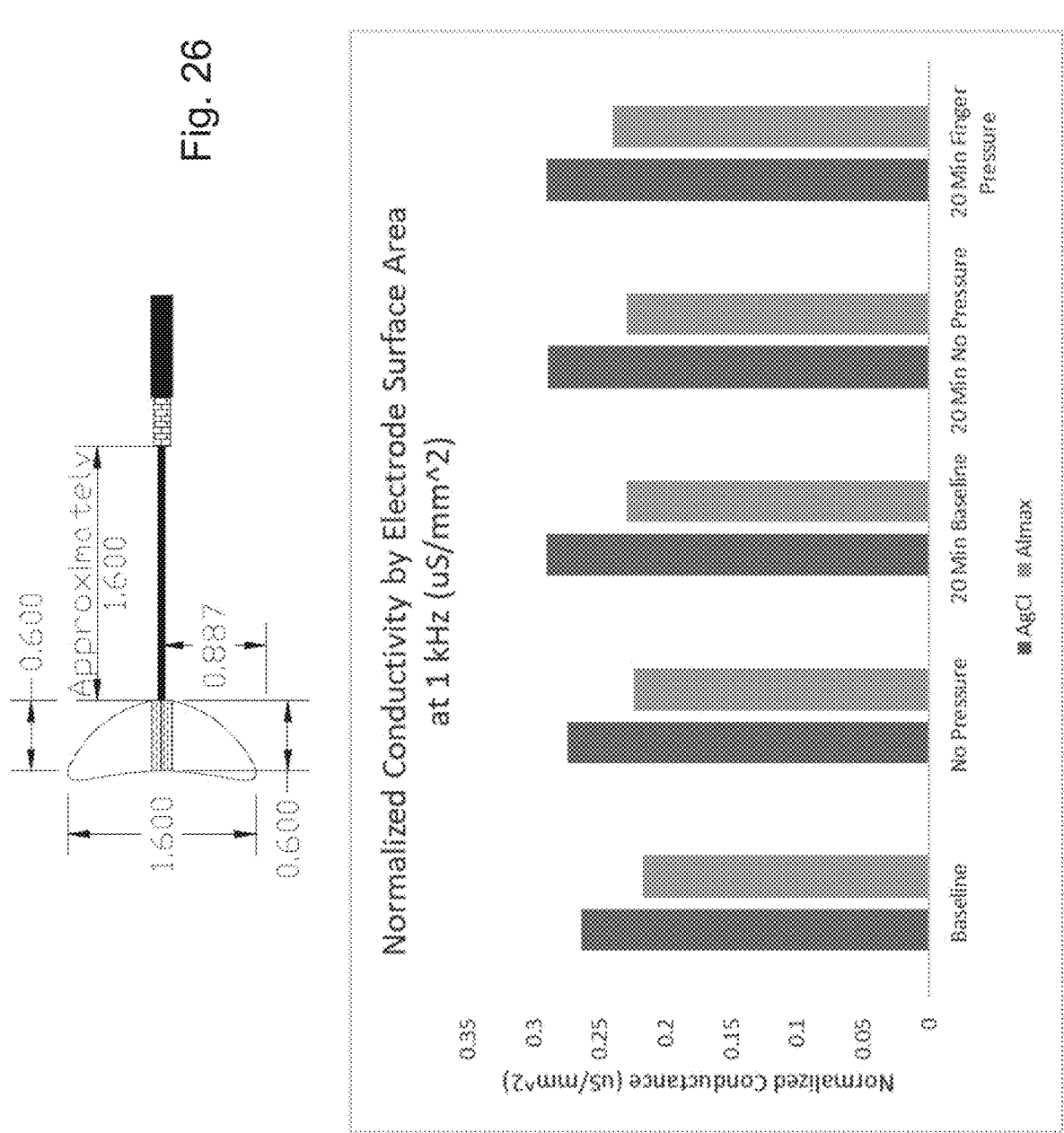
FIG. 26 is an engineering drawing of stimulation electrodes in accordance with example embodiments.
FIG. 27 is a graph showing electrode conductivity comparison at 1 kHz normalized by electrode surface area.

FIG. 26 is an engineering drawing of stimulation electrodes in accordance with example embodiments based on the measurements shown in FIG. 25. The dimensions indicated for the dome-shaped electrode contact and the electrical lead are in inches. The electrode devices may be composed of a Flexcon brand Omniwave adhesive conductive substrate on a polymer backing and the lead wire may be composed of carbon filament. The electrodes are ultra-thin (0.5 mm in this example) and therefore extremely flexible to conform precisely to the shape of the skin.

The example electrodes were tested against standard Ag/AgCl hydrogel electrodes and performed very well. FIG. 27 is a graph showing electrode conductivity comparison at 1 kHz normalized by electrode surface area based on the testing. The example custom electrodes demonstrated 81%+ 1.4% of the surface area-normalized conductivity of the Ag/AgCl standard hydrogel electrodes. While this conductivity value is somewhat lower than the standard Ag/AgCl hydrogel electrodes, the actual impedance of the custom electrodes is lower than that of the standard Ag/AgCl hydrogel electrodes because of the increased surface area contact compared to an Ag/AgCl hydrogel electrode, which requires a barrier to not allow the hydrogel to leak out and thus is less shape-adaptable.

Figure 28:
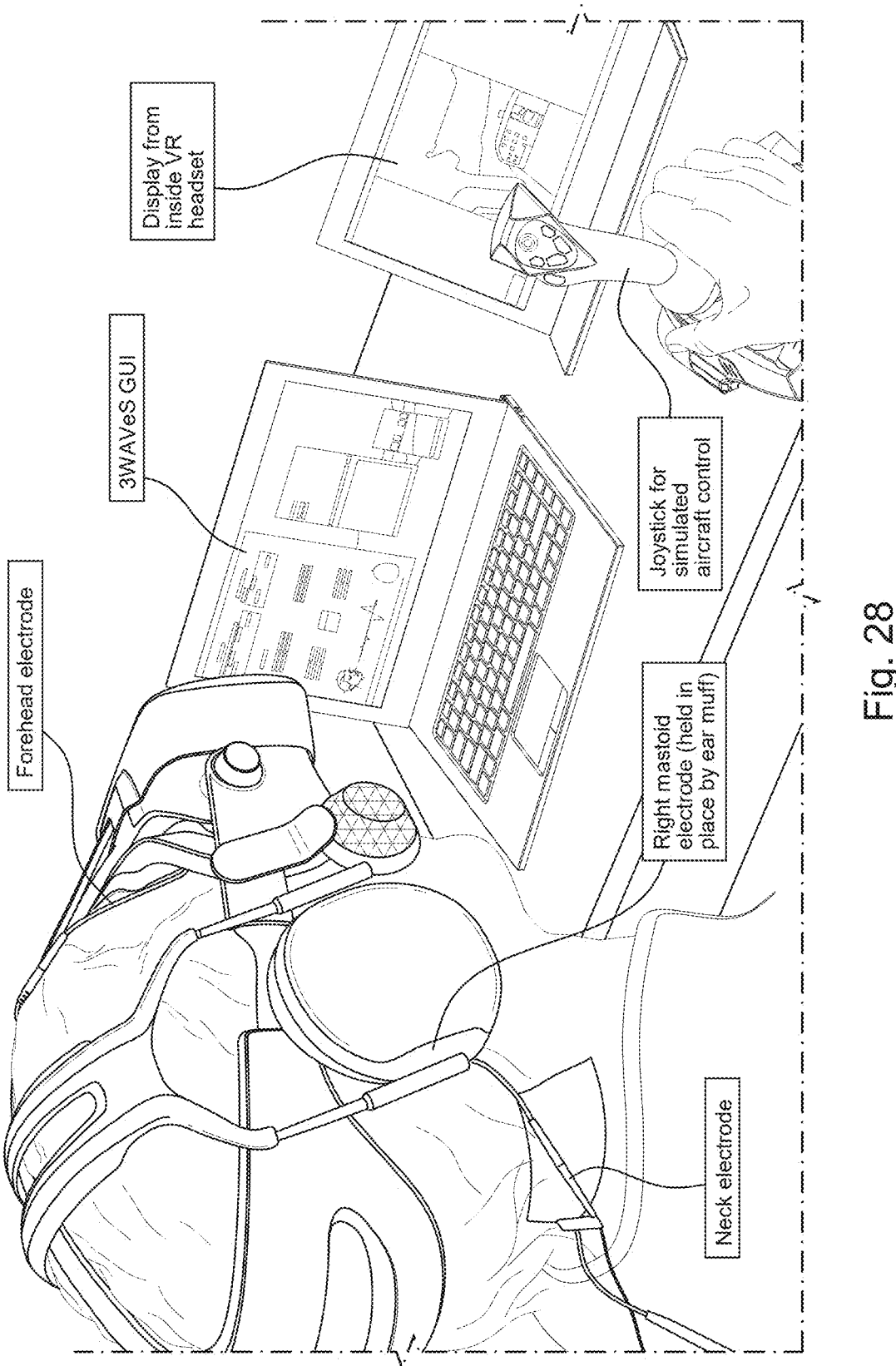
FIG. 28 shows a rendering of an example 3WAVeS system.

FIG. 28 shows a rendering up of an example 3WAVeS system with various example features labeled.

Example Applications and Advantages

Example applications for the technology described in this application include any multi-axis neural interfacing of complex signals including ocular, auditory, tactile, and vestibular interfacing. Example embodiments described above focused on multi-axis vestibular interfacing for complex and accurate stimulation of the inner ear, and in this context, the multi-axis vestibular interfacing described reduces VR-in-duced motion sickness and also increases the realism of a virtual environment. The unique ability to accurately generate multi-axis vestibular sensation can also be adapted to provide illusory sensations, thus facilitating spatial disorientation training.

One specific example application of the 3WAVeS system is to simulate spatial disorientation (SD) for pilots undergoing simulation-based training. Spatial disorientation is a persistent and dangerous factor in aviation and regularly leads to accidents. SD is generally triggered in low-visibility environments, where vestibular sensation is at odds with perceived visual cues. One spatial disorientation effect, known as "The Leans," occurs if a sustained, gradual turn is held for roughly fifteen seconds. The fluid within the semicircular canals reaches equilibrium, and the sensation of turning disappears. Due to the low turn angle, no excess seat force is sensed. Exiting the turn then results in a sensation of actually entering a turn. The Coriolis Illusion is similar, but in this situation, a rapid forward rotation of the head results in an extremely disorienting series of signals from the vestibular system. In low-visibility environments where visual cues are absent, these sensations have caused many fatal accidents.

As mentioned above, the 3WAVeS system advantageously generates disorienting vestibular sensations during simulation-based flight training. The kinematic data stream from the simulation, as well as real-time position of the user's head, are processed through a mathematical "illusory sensation transform" model, e.g., 1100 in FIG. 11, to generate sensations faithful to those which are experienced in real-life spatial disorientation scenarios, e.g., the scenarios just described above. The 3WAVeS stimulation algorithms and hardware then output these stimulation signals to the trainee. Such a stimulation can help prevent SD-related accidents by allowing aviators to become familiar with these types of sensations while in a completely safe environment.

Another example application of the 3WAVeS system noted above is in enhancing the realism of VR-based simulations. The kinematic data stream from the simulation, as well as real-time position of the user's head, are processed to generate correlating sensations of motion to the user. A major issue facing users of virtual reality headsets is "simulator sickness" which frequently causes VR users to be unable to use the headset for extended durations, thus limiting its utility as a training tool. This manifestation of motion sickness is caused by a disconnect between the visual signals being displayed in the VR headset, and the lack of motion experienced by the body; this has been described as "oculo-vestibular decoupling." Vestibular interfacing in which the motion that is visually displayed in the VR headset is replicated to the vestibular system may be used to mitigate the oculo-vestibular decoupling effect.

The 3WAVeS system overcomes the shortcomings of known vestibular stimulation techniques by permitting concurrent vestibular stimulation in 3 axes. The 3WAVeS closes the oculo-vestibular decoupling loop, and the sense of presence, or "Virtual Motion" is significantly enhanced. Enhanced reality of the virtual environment is also important, as it is critical for simulation-based training to be as realistic as possible to avoid effects such as negative training.

The technology may also be applied to passive entertainment such as film/video, where in addition to visual stimulation, the user is further immersed via vestibular stimulation.

The technology may further be applied to the healthcare field as a specific intervention for ocular, auditory, tactile, and vestibular deficiencies. For example, an individual suffering from vertigo may be treated using 3WAVeS technology with an inbuilt inertial measurement unit to override their distorted vestibular sensation, and improve balance and mobility via application of calculated, corrected vestibular signals.

Although various embodiments have been shown and described in detail, the claims are not limited to any particular embodiment or example. None of the above description should be read as implying that any particular element, step, range, or function is essential. All structural and functional equivalents to the elements of the above-described embodiments that are known to those of ordinary skill in the art are expressly incorporated herein by reference and are intended to be encompassed. Moreover, it is not necessary for a device or method to address each and every problem sought to be solved by the present invention, for it to be encompassed by the invention. No embodiment, feature, element, component, or step in this document is intended to be dedicated to the public.

All methods described herein can be performed in any suitable order unless otherwise indicated herein. The use of any and all examples, or example language (e.g., "such as") provided herein, is intended merely to better illuminate the example embodiments and does not pose a limitation on the scope of the claims appended hereto unless otherwise claimed.

As used herein, the singular forms "a," "an," and "the" may also refer to plural articles, i.e., "one or more," "at least one," etc., unless specifically stated otherwise.

The term "about" or "approximately" means an acceptable error for a particular recited value, which depends in part on how the value is measured or determined. In certain embodiments, "about" can mean 1 or more standard deviations. When the antecedent term "about" is applied to a recited range or value it denotes an approximation within the deviation in the range or value known or expected in the art from the measurements method. For removal of doubt, it is understood that any range stated herein that does not specifically recite the term "about" before the range or before any value within the stated range inherently includes such term to encompass the approximation within the deviation noted above.

What is claimed is:

1. A method for neurological interfacing with a user performed using one or more hardware data processors including processing circuitry and memory, comprising the one or more hardware data processors performing the following steps:
   receiving stimulation data from at least one data input source for stimulating two or three different axes of motion;
   processing the stimulation data to determine at least two of pitch, yaw, and roll parameters;
   based on the at least two of the pitch, yaw, and roll parameters, determining at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal;
   generating output currents based on the at least two of the yaw current signal, the pitch current signal, and the roll current signal; and applying the output currents to each of multiple electrodes positioned on the user's head to induce in the user at least two of a desired yaw sensation, a desired pitch sensation, and a desired roll sensation.

2. The method in claim 1, wherein the at least two of the yaw current signal, the pitch current signal, and the roll current signal are determined in order to reduce or avoid undesired electrical voltage gradients from being produced between two or more of the electrodes when applying the output currents to the electrodes positioned on the user's head.

3. The method in claim 1, further comprising generating feedback information based on user motion,
   wherein the processing includes processing the stimulation data and the feedback information to determine the at least two of the pitch, yaw, and roll parameters.

4. The method in claim 1, wherein two signals of the yaw current signal, the pitch current signal, and the roll current signal have the same or similar time-multiplexed modulated signals that at least substantially overlap in time, and wherein the other signal of the yaw current signal, the pitch current signal, and the roll current signal does not substantially overlap the two signals in time.

5. The method in claim 4, wherein a time-index duty cycle for the two signals is 50% of a full cycle and a time-index duty cycle for the other signal is 50% of a full cycle.

6. The method in claim 4, further comprising:
   calculating a stimulation current for each of the two signals based on a physio-electric circuit model used to calculate current sinking and sourcing at each of the multiple electrodes positioned on the user's head based on predetermined currents to be generated in each of the two signals.

7. The method in claim 4, further comprising:
   determining that a largest stimulation current of the two signals is below or equal to a threshold value, and
   eliminating a lesser of the two signals before the generating output currents step.

8. The method in claim 4, further comprising:
   determining that a largest stimulation current of the two signals is above a threshold value;
   converting the generated output currents to a current vector at each of the multiple electrodes; and
   based on the current vector at each of the multiple electrodes, determining an excess residual current and eliminating a lesser of the two signals before the generating output currents step to reduce residual current.

9. The method in claim 1, wherein the maximum current amplitude signal occurs at different times for each of at least two of the yaw current signal, the pitch current signal, and the roll current signal such that respective maximum current amplitude signals for each of the at least two of the yaw current signal, the pitch current signal, and the roll current signal do not substantially overlap in time.

10. The method in claim 9, wherein a time-index duty cycle for each of the yaw current signal, the pitch current signal, and the roll current signal is approximately one third of a full cycle.

11. The method in claim 1, further comprising:
   determining whether the stimulation data received includes three axes, two axes, or one axis of motion data;
   in response to determining that three axes of stimulation data are received, selecting first processing;
   in response to determining that two axes of stimulation data are received, selecting second processing; and in response to determining that one axis of stimulation data is received, selecting third processing, wherein the first processing, the second processing, and the third processing are different.

12. The method in claim 1, further comprising receiving the stimulation data from at least one of: a simulated environment, a memory storing pre-recorded, time-aligned visual and kinematic data, an inceptor, a smart device, and a medical device.

13. The method in claim 12, wherein the user wears a head-mounted display and the method further comprises providing external visual input to the head-mounted display from at least one of the simulated environment, the memory storing pre-recorded, time-aligned visual and kinematic data, the inceptor, the smart device, and the medical device.

14. The method in claim 13, wherein the stimulation data from the simulated environment provides angular velocity data to the one or more hardware data processors, and wherein the head-mounted display provides head angular position data to the one or more hardware data processors, the one or more hardware data processors processing the angular velocity data and the head angular position data to determine the at least two of pitch, yaw, and roll parameters.

15. The method in claim 13, wherein the stimulation data from the memory storing pre-recorded, time-aligned visual and kinematic data is processed to provide angular velocity data to the one or more hardware data processors, and wherein the head-mounted display provides head angular position data to the one or more hardware data processors, the one or more hardware data processors processing the angular velocity data and the head angular position data to determine the at least two of pitch, yaw, and roll parameters.

16. The method in claim 13, wherein the stimulation data from the inceptor provides interceptor vector magnitude data to the one or more hardware data processors, wherein the head-mounted display receives external visual input, and the one or more hardware data processors process the interceptor vector magnitude data to determine the at least two of pitch, yaw, and roll parameters.

17. The method in claim 13, further comprising:

transforming the at least two of pitch, yaw, and roll parameters to generate an illusory vestibular signal that is based on an analytical model of how the human vestibular system adapts to constant angular velocity.

18. The method in claim 1, further comprising adjusting, by a user interface, the at least two of pitch, yaw, and roll parameters prior to the determining of the at least two of the yaw current signal, the pitch current signal, and the roll current signal.

19. A system for neurological interfacing with a user, comprising:

one or more hardware data processors including processing circuitry and memory;

the one or more hardware data processors configured to:

receive stimulation data from at least one data input source for stimulating two or three different axes of motion;

process the stimulation data to determine at least two of pitch, yaw, and roll parameters;

based on the at least two of the pitch, yaw, and roll parameters, determine at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal;

generate output currents based on the least two of the yaw current signal, the pitch current signal, and the roll current signal; and apply the output currents to each of multiple electrodes positioned on the user's head to induce in the user at least two of a desired yaw sensation, a desired pitch sensation, and a desired roll sensation.

20. The system in claim 19, wherein the one or more hardware data processors is configured to determine the at least two of the yaw current signal, the pitch current signal, and the roll current signal in order to reduce or avoid undesired electrical voltage gradients from being produced between two or more of the electrodes when applying the output currents to the electrodes positioned on the user's head.

21. The system in claim 19, wherein the one or more hardware data processors is configured to process the stimulation data and feedback information that is based on user motion to determine the at least two of the pitch, yaw, and roll parameters.

22. The system in claim 19, wherein two signals of the yaw current signal, the pitch current signal, and the roll current signal have the same or similar time-multiplexed modulated signals that at least substantially overlap in time, and wherein the other signal of the yaw current signal, the pitch current signal, and the roll current signal does not substantially overlap the two signals in time.

23. The system in claim 22, wherein a time-index duty cycle for the two signals is 50% of a full cycle and a time-index duty cycle for the other signal is 50% of a full cycle.

24. The system in claim 22, wherein the one or more hardware data processors is configured to calculate a stimulation current for each of the two signals based on a physio-electric circuit model used to calculate current sinking and sourcing at each of the multiple electrodes positioned on the user's head based on predetermined currents to be generated in each of the two signals.

25. The system in claim 22, wherein the one or more hardware data processors is configured to:

determine that a largest stimulation current of the two signals is below or equal to a threshold value, and eliminate a lesser of the two signals before generating output currents.

26. The system in claim 22, wherein the one or more hardware data processors is configured to:

determine that a largest stimulation current of the two signals is above a threshold value;

convert the generated output currents to a current vector at each of the multiple electrodes; and based on the current vector at each of the multiple electrodes, determine an excess residual current and eliminate a lesser of the two signals before generating output currents to reduce residual current.

27. The system in claim 19, wherein the maximum current amplitude signal occurs at different times for each at least two of the yaw current signal, the pitch current signal, and the roll current signal such that respective maximum current amplitude signals for each of the at least two of the yaw current signal, the pitch current signal, and the roll current signal do not substantially overlap in time.

28. The system in claim 27, wherein a time-index duty cycle for each of the yaw current signal, the pitch current signal, and the roll current signal is approximately one third of a full cycle.

29. The system in claim 19, further comprising:

an interface configured to receive output current values from the one or more hardware data processors corresponding to at least two of a yaw current signal, a pitch current signal, and a roll current signal, the one or more hardware data processors configured to communicate with the interface;

one or more control processors configured to communicate with the interface;

multiple current sources, each current source corresponding to and configured to provide a stimulation current to a stimulation electrode positioned on a user's head based on a corresponding one of the output current values;

multiple relays, each relay coupled to a corresponding one of the current sources and configured to selectively disconnect the corresponding current source from delivering a stimulation current to a corresponding electrode when a stimulation scenario requires that one or more electrodes be disconnected; and wherein the one or more control processors is configured to apply a stimulation current to at least some of multiple electrodes positioned on the user's head to induce in the user at least two of a desired yaw sensation, a desired pitch sensation, and a desired roll sensation.

30. The system in claim 29, further comprising:

multiple fuses, each fuse located between a corresponding one of the current sources and a corresponding electrode to protect against delivering a current to the user in excess of a maximum current value.

31. A system for neurological interfacing with a user, comprising:

an interface configured to receive output current values corresponding to at least two of a yaw current signal, a pitch current signal, and a roll current signal;

one or more control processors communicating with the interface;

multiple current sources, each current source corresponding to and configured to provide a stimulation current to a stimulation electrode positioned on a user's head based on a corresponding one of the output current values;

multiple relays, each relay coupled to a corresponding one of the current sources and configured to selectively disconnect the corresponding current source from delivering a stimulation current to a corresponding electrode when a stimulation scenario requires that one or more electrodes be disconnected; and wherein the one or more control processors is configured to apply a stimulation current to at least some of multiple electrodes positioned on the user's head to induce in the user at least two of a desired yaw sensation, a desired pitch sensation, and a desired roll sensation.

32. The system for neurological interfacing with a user in claim 31, further comprising:

multiple fuses, each fuse located between a corresponding one of the current sources and a corresponding electrode to protect against delivering a current to the user in excess of a maximum current value.

33. The system for neurological interfacing with a user in claim 31, further comprising:

one or more optoisolators configured to isolate signals provided to the one or more control processors and to the multiple relays.

34. The system for neurological interfacing with a user in claim 31, further comprising one or more hardware data processors is configured to:

receive stimulation data from at least one data input source for stimulating two or three different axes of motion;

process the stimulation data to determine at least two of pitch, yaw, and roll parameters;

based on the at least two of the pitch, yaw, and roll parameters, determine at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal; and generate the output current values based on the least two of the yaw current signal, the pitch current signal, and the roll current signal and provide the output currents to the interface.

35. The system for neurological interfacing with a user in claim 31, further comprising one or more hardware data processors is configured to determine the at least two of the yaw current signal, the pitch current signal, and the roll current signal in order to reduce or avoid undesired electrical voltage gradients from being produced between two or more of the electrodes when applying the output currents to the electrodes positioned on the user's head.

36. The system for neurological interfacing with a user in claim 31, wherein two signals of the yaw current signal, the pitch current signal, and the roll current signal have the same or similar time-multiplexed modulated signals that at least substantially overlap in time, and wherein the other signal of the yaw current signal, the pitch current signal, and the roll current signal does not substantially overlap the two signals in time.

37. The system for neurological interfacing with a user in claim 31, wherein the maximum current amplitude signal occurs at different times for each at least two of the yaw current signal, the pitch current signal, and the roll current signal such that respective maximum current amplitude signals for each of the at least two of the yaw current signal, the pitch current signal, and the roll current signal do not substantially overlap in time.

38. A non-transitory, computer readable storage medium storing program instructions, which when executed by one or more hardware data processors, cause the one or more hardware data processors to perform the following method for neurological interfacing with a user:

receiving stimulation data from at least one data input source for stimulating two or three different axes of motion;

processing the stimulation data to determine at least two of pitch, yaw, and roll parameters;

based on the at least two of the pitch, yaw, and roll parameters, determining at least two of a yaw current signal, a pitch current signal, and a roll current signal, wherein the at least two of the yaw current signal, the pitch current signal, and the roll current signal are time-multiplexed modulated signals, where a maximum current amplitude signal occurs at different times for the at least two of the yaw current signal, the pitch current signal, and the roll current signal;

generating output currents based on the at least two of the yaw current signal, the pitch current signal, and the roll current signal; and applying the output currents to each of multiple electrodes positioned on the user's head to induce in the user at least two of a desired yaw sensation, a desired pitch sensation, and a desired roll sensation.

\* \* \* \* \*